United States Patent [19]
Barbachyn et al.

[11] Patent Number: 6,090,820
[45] Date of Patent: Jul. 18, 2000

[54] SPIROCYCLIC AND BICYCLIC DIAZINYL AND CARBAZINYL OXAZOLIDINONES

[75] Inventors: Michael Robert Barbachyn, Kalamazoo, Mich.; Steven Joseph Brickner, Ledyard, Conn.; Douglas K. Hutchinson, Kalamazoo, Mich.

[73] Assignee: Pharmacia & Upjohn Company, Kalamazoo, Mich.

[21] Appl. No.: 09/202,195

[22] PCT Filed: Apr. 18, 1996

[86] PCT No.: PCT/US96/05202

§ 371 Date: Nov. 7, 1997

§ 102(e) Date: Nov. 7, 1997

[87] PCT Pub. No.: WO96/35691

PCT Pub. Date: Nov. 14, 1996

Related U.S. Application Data

[63] Continuation of application No. 08/438,705, May 11, 1995, abandoned.

[51] Int. Cl.⁷ ..................... A61K 31/422; A61K 31/437; C07D 487/04
[52] U.S. Cl. ................. 514/300; 514/376; 546/113; 548/232
[58] Field of Search ............... 546/113; 548/232; 514/300, 376

[56] References Cited

U.S. PATENT DOCUMENTS

| | | | |
|---|---|---|---|
| 4,801,600 | 1/1989 | Wang et al. | 514/376 |
| 4,921,869 | 5/1990 | Wang et al. | 514/376 |

FOREIGN PATENT DOCUMENTS

| | | | |
|---|---|---|---|
| 312000 | 4/1989 | European Pat. Off. | C07D 263/20 |
| 316594 | 5/1989 | European Pat. Off. | C07D 263/20 |
| 352781 | 1/1990 | European Pat. Off. | C07D 263/20 |
| PCT/US89/03548 | 3/1990 | WIPO | C07D 413/04 |
| PCT/US92/08267 | 4/1993 | WIPO | C07D 263/20 |
| PCT/US93/03570 | 11/1993 | WIPO | C07D 263/20 |
| PCT/US94/8904 | 3/1995 | WIPO | C07D 263/220 |
| WO 95 25106 | 9/1995 | WIPO | C07D 413/10 |

OTHER PUBLICATIONS

Gregory W. A., et al., *J. Med. Chem.*, 32, 1673–81 (1989).
Gregory W. A., et al., *J. Med. Chem.*, 33, 2569–78 (1990).
Wang C., et al., *Tetrahedron*, 45, 1323–26 (1989).
Brittelli, et al., *J. Med. Chem.*, 35, 1156–1165 (1992).

*Primary Examiner*—Laura L. Stockton
*Attorney, Agent, or Firm*—Andrew M. Solomon

[57] ABSTRACT

A compound of structural Formula I or II which is useful for treating microbial infections in humans or other warm-blooded animals, or pharmaceultically acceptable salts thereof as defined herein.

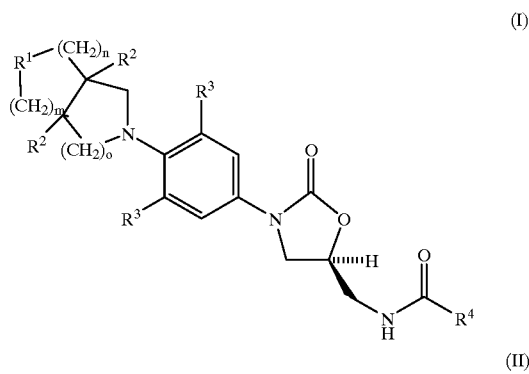

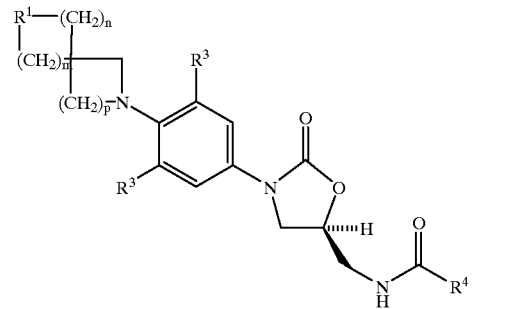

11 Claims, No Drawings

SPIROCYCLIC AND BICYCLIC DIAZINYL AND CARBAZINYL OXAZOLIDINONES

This application is the national phase of international application PCT/US96/05202, International Filing date Apr. 18, 1996, which was a continuation of U.S. application Ser. No. 08/438,705, filed May 11, 1995, now abandoned.

BACKGROUND OF THE INVENTION

The subject invention discloses new and useful oxazolidinones having a spirocyclic or bicyclic diazinyl or carbazinyl moiety. The compounds are useful antimicrobial agents effective against a number of human and veterinary pathogens, including gram-positive aerobic bacteria such as multiply-resistant staphylococci, streptococci and enterococci as well as anerobic organisms such as Bacteroides spp. and Clostridia spp. species, and acid-fast organisms such as *Mycobacterium tuberculosis* and other mycobacterial species.

Information Disclosure

The present compounds are related by their phenyloxazolidinone ring structure to those disclosed in the publications below except that the subject compounds have a spirocyclic or bicyclic diazinyl or carbazinyl moiety. The instant compounds have useful antibacterial activity.

PCT/US94/08904 application discloses oxazolidinone antibacterial compounds having either a morpholine or thiomorpholine substituent.

PCT/US93/03570 application discloses oxazolidinones containing a substituted diazine moiety and their uses as antimicrobials.

PCT/US92/08267 application discloses substituted aryl and heteroaryl-phenyl-oxazolidinones useful as antibacterial agents.

PCT/US89/03548 application discloses 5'indolinyl-5β-amidomethyloxazolidin-ones, 3-(fused-ring substituted)phenyl-5β-amidomethyloxazolidinones, and 3-(nitrogen substituted)phenyl-5β-amidomethyloxazolidinones which are useful as antibacterial agents.

Other references disclosing various oxazolidinones include U.S. Pat. No. 4,801,600, 4,921,869, Gregory W. A., et al., *J. Med. Chem.*, 32, 1673–81 (1989); Gregory W. A., et al., *J. Med. Chem.*, 33, 2569–78 (1990); Wang C., et al., *Tetrahedron*, 45, 1323–26 (1989); and Brittelli, et al., *J. Med. Chem.*, 35, 1156 (1992).

European Patent Publication 352,781 discloses phenyl and pyridyl substituted phenyl oxazolidinones.

European Patent Publication 316,594 discloses 3-substituted styryl oxazolidinones.

European Patent Publication 312,000 discloses phenylmethyl and pyridinylmethyl substituted phenyl oxazolidinones.

SUMMARY OF THE INVENTION

In one aspect the subject invention is a compound of structural Formula I:

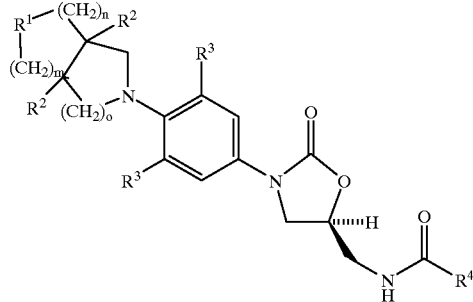

Formula I

In another aspect the subject invention is composed of structural Formula II:

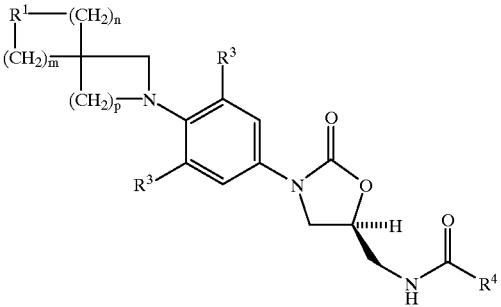

Formula II or pharmaceutically acceptable salts thereof wherein:

$R^1$ is (a) $NR^5$,
(b) $CR^6R^7$;

$R^2$ is independently H or $CH_3$;

$R^3$ is independently H, F, Cl or methoxy;

$R^4$ is (a) hydrogen,
(b) $C_1$–$C_8$ alkyl (optionally substituted with one or more of the following: F, Cl, hydroxy, $C_1$–$C_8$ alkoxy, $C_1$–$C_8$ acyloxy),
(c) $C_3$–$C_6$ cycloalkyl,
(d) amino,
(e) $C_1$–$C_8$ alkylamino,
(f) $C_1$–$C_8$ dialkylamino,
(g) $C_1$–$C_8$ alkoxy;

is (a) H,
(b) $C_{1-6}$ alkyl (optionally substituted with one or more of the following: Cl, F, CN, OH, $C_{1-4}$ alkoxy, amino, hydroxylamino, alkoxylamino, $C_{1-4}$ acyloxy, $C_{1-4}$ alkylsulfenyl, $C_{1-4}$ alkylsulfinyl, $C_{1-4}$ alkylsulfonyl, aminosulfonyl, $C_{1-4}$ alkylaminosulfonyl, $C_{1-4}$ dialkylaminosulfonyl, 4-morpholinylsulfonyl, phenyl (optionally substituted with one or more of F, Cl, CN, OH, $C_1$–$C_4$alkoxy), 5-isoxazolyl, ethenyloxy, ethynyl),
(c) $C_{1-6}$ acyl (optionally substituted with one or more of the following: Cl, F, OH, SH, $C_{1-4}$ alkoxy, naphthalenoxy and phenoxy (optionally substituted with one or more of the following: Cl, F, OH, $C_1$–$C_4$alkoxy, amino, $C_1$–$C_4$acylamino, $C_1$–$C_4$alkyl), amino, $C_1$–$C_4$acylamino, hydroxylamino, alkoxylamino, $C_{1-4}$ acyloxy, phenyl, $C_1$-$C_4$alkylcarbonyl, $C_1$-$C_4$alkylamino, $C_1$-$C_4$dialkylamino, $C_1$-$C_4$hydroxyacyloxy, $C_1$-$C_4$alkylsulfenyl, phthalimido, maleimido, succinimido), (d) $C_{1-6}$ alkylsulfonyl (optionally substituted with one or more of the following: Cl, F, OH, $C_{1-4}$ alkoxy, amino, hydroxylamino, alkoxylamino, $C_{1-4}$ acyloxy, phenyl), (e) arylsulfonyl (optionally substituted with one or more of the following: F, Cl, $OCH_3$, OH or $C_{1-4}$ alkyl), (f) $C_{1-6}$ alkoxycarbonyl (optionally substituted with one or more of the following: Cl, F, OH, $C_{1-4}$ alkoxy, $C_{1-4}$ acyloxy, phenyl), (g) aminocarbonyl, $C_{1-6}$ alkylaminocarbonyl or $C_{1-6}$ dialkylaminocarbonyl (where the alkyl groups are optionally substituted with one or more of the following: Cl, F, OH, $C_{1-4}$ alkoxy, phenyl), (h) five- and six-membered heterocycles, especially 2-oxazolyl, 2-thiazolyl, 3-isoxazolyl, 3-isothiazolyl and dihydro derivatives of these ring systems (all optionally substituted with one or more of the following: Cl, F, OH, amino, $C_{1-4}$acylamino, $C_{1-4}$ alkylsulfonylamino, $C_{1-4}$ alkoxycarbonylamino, $C_{1-4}$ alkoxy, $C_{1-4}$ acyloxy, $C_{1-4}$alkyl which can be substituted with F, OH or $C_{1-4}$ alkoxy, (i) $C_3$-$C_6$ cycloalkylcarbonyl (optionally substituted with one or more of the following: F, Cl, OH, $C_1$-$C_4$alkoxy, CN), (j) benzoyl (optionally substituted with one or more of the following: F, Cl, OH, $C_1$-$C_4$alkoxy, $C_1$-$C_4$alkyl, amino, $C_1$-$C_4$acylamino), (k) pyrtolylcarbonyl (optionally substituted with one or more of $C_1$-$C_4$alkyl), (l) $C_1$-$C_2$ acyloxyacetyl (acyl optionally substituted with the following: amino, $C_1$-$C_4$alkylamino, $C_1$-$C_4$dialkylamino, 4-morpholino, 4-aminophenyl, 4-(dialkylamino)phenyl, 4-(glycylamino)phenyl);

$R^6$ is (a) H,
(b) OH,
(c) $C_{1-6}$ alkoxy,
(d) amino, $C_{1-6}$ alkylamino, $C_{1-6}$ dialkylamino, hydroxylamino, or $C_{1-2}$ alkoxylamino (all of which can be optionally substituted on the nitrogen with: $C_{1-6}$ acyl optionally substituted with one-two of Cl or OH, $C_{1-6}$ alkylsulfonyl optionally substituted with one-two of Cl or OH, $C_{1-6}$ alkoxycarbonyl),
(e) Cl or F;

$R^7$ is (a) H,
(b) $C_{1-6}$ alkyl (optionally substituted with one or more of the following: Cl, F, CN, OH, $C_{1-4}$ alkoxy, $C_{1-4}$ acyloxy, amino),
(c) CN,
(d) phenyl (optionally substituted with one or more of the following: Cl, F, OH, $C_{1-4}$ alkoxy); or $R^6$ and $R^7$ taken together are (a) carbonyl or thiocarbonyl group,
(b) ethylene ketal (—$OCH_2CH_2O$—), propylene ketal (—$OCH_2CH_2CH_2O$—), ethylene thioketal (—$SCH_2CH_2S$—), propylene thioketal (—$SCH_2CH_2CH_2S$—), dimethyl ketal, diethyl ketal, dimethyl thioketal and diethyl thioketal,
(c) oxime (optionally substituted with H, $C_{1-6}$ alkyl (optionally substituted with Cl, F or $C_{1-4}$ alkoxy), $C_{1-6}$ acyl (optionally substituted with one or more of the following: Cl, F, OH, $C_{1-4}$ alkoxy, $C_{1-4}$ acyloxy),
(d) hydrazone (optionally substituted with H, $C_{1-6}$ aLkyl (optionally substituted with one or more Cl, F, OH, $C_{1-4}$ alkoxy, $C_{1-4}$ acyloxy, phenyl, $C_{1-6}$ acyl (optionally substituted with one or more of Cl, F, OH, $C_{1-4}$ alkoxy, $C_{1-4}$ acyloxy, phenyl), $C_{1-6}$ alkoxycarbonyl (optionally substituted with one or more of the following: Cl, F, OH, $C_{1-4}$ alkoxy, $C_{1-4}$ acyloxy, phenyl), $C_{1-6}$ alkylsulfonyl,
(e) imine (optionally substituted with H or a $C_{1-6}$ alkyl (optionally substituted with Cl, F, OH, $C_{1-4}$ alkoxy, $C_{1-4}$ acyloxy, phenyl),
(f) carbon-carbon double bond (optionally substituted with H, $C_{1-4}$ alkoxycarbonyl, $C_{1-4}$ alkyl (optionally substiuted with Cl, F, OH, $C_{1-4}$ alkoxy, phenyl);

m is 0–2;

n is 1–3;

o is 0–3; and p is 1–3.

In another aspect, the subject invention is directed toward a method for treating microbial infections in humans or other warm-blooded animals by administering to a patient in need thereof an effective amount of a compound of Formula I or II as described above. The compound can be administered in a pharmaceutical composition either orally, parenterally or topically. Preferably the compound is administered orally or parenterally in an amount of from about 0.1 to about 100 mg/kg of body weight/day, more preferably, from about 3.0 to about 50 mg/kg of body weight/day.

DETAILED DESCRIPTION OF THE INVENTION

The present invention discloses novel spirocyclic and fused bicyclic diazinyl and carbazinyl oxazolidinones of structural Formula I and II as described above. The compounds are useful antimicrobial agents, effective against a number of human and veterinary pathogens, particularly aerobic gram-positive bacteria, including multiply-resistant staphylococci, streptococci and enterococci, as well as anaerobic organisms such as bacteroides and clostridia species, and acid-fast bacteria such as as *Mycobacterium tuberculosis* and other mycobacterial species.

The R groups are as set forth above. As used herein the term $C_{n-m}$ is inclusive such that a compound of $C_{1-8}$ would include compounds of one to 8 carbons and their isomeric forms. The various carbon moieties are defined as follows: Alkyl refers to an aliphatic hydrocarbon radical and includes branched or unbranched forms such as methyl, ethyl, n-propyl, i-propyl, n-butyl, i-butyl, s-butyl, t-butyl, n-pentyl, i-pentyl, neo-pentyl, n-hexyl, i-hexyl, n-heptyl, i-heptyl and n-octyl. Acyl refers to those having one to six carbon atoms such as formyl, acetyl, propionyl, etc. and their isomeric forms.

The $R^3$ substituents are preferably both fluorine and, more preferably, fluorine and hydrogen.

The $R^4$ substituent is preferably hydrogen, methyl, difluoromethyl, dichloromethyl, hydroxymethyl or methoxy. More preferably $R^4$ is methoxy, difluoromethyl, dichloromethyl or methyl. It is most preferred that $R^4$ is methyl.

The $R^5$ substituent is preferably hydroxyacetyl.

The preferred absolute configuration at C-5 of the oxazolidinone ring of compounds claimed in this invention is as represented in the structures of Formula I and II. This absolute configuration is called (S) under the Cahn-Ingold-Prelog nomenclature system. It is this (S)-enantiomer which is pharmacologically active. The racemic mixture is useful in the same way and for the same purpose as the pure (S)-enantiomer; the difference is that twice as much racemic material must be used to produce the same antibacterial effect. It will be apparent to one skilled in the art that when a chiral center is present in the diazinyl or carbazinyl fragment of compounds of structural Formula I and II, then diastereomers are possible. These diastereomers, in racemic and enantiomerically enriched forms, are also within the scope of the compounds of Formula I and II of the invention.

Both organic and inorganic acids can be employed to form non-toxic pharmaceutically acceptable acid addition salts of the compounds of this invention, where applicable. Illustrative acids are sulfuric, nitric, phosphoric, hydrochloric, citric, acetic, lactic, tartaric, pamoic, ethanedisulfonic, sulfamic, succinic, cyclohexylsulfamic, fumaric, maleic, and benzoic acid. These salts are readily prepared by methods known in the art.

Pharmaceutical compositions of this invention may be prepared by combining the compounds of Formula I or II with a solid or liquid pharmaceutically acceptable carrier and, optionally, with pharmaceutically acceptable adjuvants and excipients employing standard and conventional techniques. Such pharmaceutical compositions can then be used in treating microbial infections in humans or other warm-blooded animals (patients) by various routes of administration in an effective amount or therapeutically effective amount. Typical amounts can be from about 0.1 to about 100 mg/kg of body weight/day, more preferably, from about 3.0 to about 50 mg/kg of body weight/day.

Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound of Formula I according to this invention.

The quantity of active component, that is the compound of Formula I or II according to this invention, in the pharmaceutical composition and unit dosage form thereof may be varied or adjusted widely depending upon the particular application, the potency of the particular compound, the desired concentration. Generally, the quantity of active component will range between 0.5% to 90% by weight of the composition.

In therapeutic use for treating, or combatting, bacterial infections in warm-blooded animals, the compounds or pharmaceutical compositions thereof will be administered orally and/or parenterally at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood level or the initial dosage may be smaller than the optimum and the daily dosage may be progressively increased during the course of treatment depending on the particular situation. If desired, the daily dose may also be divided into multiple doses for administration, e.g., two to four times per day.

The compounds of Formula I or II according to this invention are administered parenterally, i.e., by injection, for example, by intravenous injection or by other parenteral routes of administration. Pharmaceutical compositions for parenteral administration will generally contain a pharmaceutically acceptable amount of the compound according to Formula I or II as a soluble salt (acid addition salt or base salt) dissolved in a pharmaceutically acceptable liquid carrier such as, for example, water-for-injection and a buffer to provide a suitably buffered isotonic solution, for example, having a pH of about 3–7. Suitable buffering agents include, for example, trisodium orthophosphate, sodium bicarbonate, sodium citrate, N-methylglucamine, L(+)-lysine and L(+)-arginine to name but a few representative buffering agents. The compound according to Formula I or II generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage.

A method of preparation of oxazolidinones of Formula I and II in enantiomerically pure form is depicted in Charts I–VI.

As shown in Chart I, fused bicyclic diazines and carbazines of structure 1 are known in the literature. EP 0 350 733 A2. Dave, P. R.; Forohar, F.; Axenrod, T.; Qi, L.; Watnick, C.; Yazdekhasti, H. Tetrahedron Lett. 1994, 35, 8965. Jacquet, J.-P.; Bouzard, D.; Kiechel, J.-R.; Remuzon, P. Tetrahedron Lett. 1991, 32, 1565. JP 8956 673. Chem. Abstr. 1989, 111, 153779w. Loftus, P.; et al. J. Heterocycl. Chem. 1983, 20, 321. Gobeaux, B.; Ghosez, L. Heterocycles 1989, 28, 29. Xu, W.; Zhang, X.-M.; Mariano, P. S. J. Am. Chem. Soc. 1991, 113, 8863. In addition, spirocyclic diazines and carbazines of structure 2 are also known substances. Culbertson, T. P.; Sanchez, J. P.; Gambino, L.; Sesnie, J. A. J. Med. Chem. 1990, 33, 2270. Domagala, J. M.; et al. U.S. Pat. No. 4 638 067, 1987. Xu, W.; Zhang, X.-M.; Mariano, P. S. J. Am. Chem. Soc. 1991, 113, 8863.

Charts II–VI outline the synthesis of oxazolidinone antibacterial agents of structural Formula I and II from diazines or carbazines 1 and 2.

As shown in Chart II, diazine or carbazine 1 is reacted with a functionalized nitrobenzene 3 (X=halogen or trifluoromethanesulfonate) in the presence of a suitable base/solvent combination, for example dibasic potassium phosphate in dimethyl sulfoxide or N,N-diisopropylethylamine in acetonitrile or THF, and at a suitable temperature, typically ambient temperature to 70° C., to afford the adduct 4. It will be apparent to one skilled in the art that the $R^1$ residue of compound 1 might require the presence of a suitable protecting group. For example, in the diazine case, where $R^1$ is nitrogen, the benzyl protecting group was found to be effective at blocking this position. Alternatively, in the case of carbazine variants (R $_1$=functionalized carbon) sensitive groups such as a hydroxyl group can be protected as their tert-butyldimethylsilyl ethers. In the case where $R^1$ is a carbonyl, prior conversion to a ketal protects this functional group from subsequent chemical conversions. It will be apparent to those skilled in the art that these protecting groups are merely representative and that alternative protecting groups, such as those described in Greene, T. W.; Wuts, P. G. M. "Protective Groups in Organic Synthesis", 2nd ed.; John Wiley & Sons: New York, 1991, can be employed. The nitro group of 4 is then reduced by catalytic hydrogenation in the presence of a suitable catalyst, such as 10% palladium/carbon or W-2 Raney nickel, and in an appropriate solvent, for example THF/$H_2O$. When this latter solvent system is utilized, the reaction mixture is first filtered to remove the catalyst and the filtrate containing the intermediate aniline is then treated with, for example, sodium bicarbonate and benzyl or methyl chloroformate to give the corresponding benzyl ($R=CH_2Ph$) or methyl ($R=CH_3$) urethane derivatives 5. When $R^1$ is a benzylamino residue, the benzyl group is lost under the hydrogenation conditions and is replaced, for example, with a Cbz group during the subsequent urethane forming reaction. The urethanes 5 are then deprotonated with a suitable base such as n-butyllithium (n-BuLi), lithium diisopropylamide (LDA) or lithium bis(trimethylsilyl) amide, in a suitable solvent such as tetrahydrofuran (THF) and at a suitable temperature such as −78 to −60° C. to give a lithiated intermediate which is then treated with commercially available (−)-(R)-glycidyl butyrate. Warming to ambient temperature then directly affords the 5-(hydroxymethyl) oxazolidinones 6 in enantiomerically enriched form.

As shown in Chart III, compound 6 is then converted to the corresponding mesylate 7 (R=methyl) or aryl sulfonate 7 ($R=ArSO_2$, for example p-toluenesulfonyl) by the action of, for example, methanesulfonyl chloride/pyridine or methanesulfonyl chloride/triethylamine/dichloromethane or p-toluenesufonyl chloride/pyridine. The resultant sulfonate derivative 7 is then reacted with an azide source such as sodium or potassium azide in an aprotic solvent such as N,N-dimethylformamide (DMF) or 1-methyl-2-pyrrolidinone optionally in the presence of a catalyst such as 18-crown-6 at a temperature of 50–90° C. to afford the azide 8. The azide is then reduced by hydrogenation with palladium on carbon or a platinum catalyst in an appropriate solvent such as ethyl acetate or methanol to give the corresponding amine 9. Alternatively, the azide 8 can be reduced by treatment with a trivalent phosphorus compound such as triphenylphosphine in a suitable solvent such as tetrahydrofuran followed by the addition of water. The intermediate amine 9 may also be prepared by treatment of the phthalimide derivative 10 (obtained by reacting sulfonate 7 with potassium phthalimide in a suitable solvent, for example, acetonitrile at reflux temperature) with methylamine in ethanol/$H_2O$ at reflux temperature. Alternatively, the amine 9 may be prepared directly from the mesylate 7 by ammonolysis in a solvent system consisting of $H_2O$/ispropanol/THF in a sealed reaction vessel immersed in a 70–95° C. oil bath. The amine 9 is then acylated by reactions known to those skilled in the art to give oxazolidinones of structure 11. For example, the amine can be reacted with an acid chloride or anhydride in a basic solvent such as pyridine at a temperature ranging from −30 to 30° C. to provide the acylated compound 11 ($R^4$=optionally substituted alkyl). It will be apparent to one skilled in the art that other carbonyl groups within the scope of this invention can be readily appended to the amine 9 by standard acylation techniques, for example those highlighted in March, J. "Advanced Organic Chemistry", 3rd ed.; John Wiley & Sons: New York, 1985; p 370–375, to give additional examples of 11. The oxazolidinones 11 are examples of structural Formula I, which are the subject of this invention.

As shown in Charts IV and V, selected examples of the fused bicyclic diazine and carbazine containing oxazolidinones 11, themselves antibacterial agents of structural Formula I, can be further elaborated to additional compounds of Formula I.

Compound 12 (see Chart IV), efficiently obtained by catalytic hydrogenolysis of the corresponding Cbz protected derivative 11 ($R^1$=CbzN), can be N-alkylated by procedures known to one skilled in the art, including treatment of 12 with alkyl halides or tosylates in the presence of a suitable base, to furnish compounds 13. Alternatively, selected alkyl groups can be appended on the nitrogen of 12 by a reductive alkylation procedure as described in March, J. "Advanced Organic Chemistry", 4th ed.; John Wiley & Sons: New York, 1992; p 898–900. Compound 12 can also be converted to various acylated derivatives 14 by treatment of 12 with various carbonyl derivatives, such as acid chlorides, anhydrides and the like, in the presence of appropriate bases, and in suitable solvents known to one skilled in the art. Similarly, sulfonamide derivatives 15 are prepared by reacting 12 with alkyl- and arylsulfonyl chlorides in the presence of suitable amine bases and in appropriate solvents known to one skilled in the art. Urethanes 16 are prepared from compound 12 through the action of chloroformates and the like in the presence of appropriate bases and in suitable solvent systems known to one skilled in the art. The above discussion should be considered merely representative in nature, since other derivatives of 12 are possible, for example the reaction of 12 with an isocyanate to give ureas 14 (R=NHY, where Y is an optionally substituted alkyl or phenyl group). Compounds 12–16 are fused bicyclic diazine examples of structural Formula I, which are the subject of this invention.

Compound 17 (see Chart V), readily obtained from ketal 11 [$R^1$=C(OCH$_2$CH$_2$O)] by acidic hydrolysis, for example with p-toluenesulfonic acid in acetone/water, can be further elaborated to additional examples of structural Formula I. For example, various hydrazone derivatives 18 can be prepared by reacting 17 with hydrazines, as described in Greene, T. W.; Wuts, P. G. M. "Protective Groups in Organic Synthesis", 2nd ed.; John Wiley & Sons: New York, 1991, p 212–213 and March, J. "Advanced Organic Chemistry", 4th ed.; John Wiley & Sons: New York, 1992; p 904–905. Oximes 19 are readily prepared by reacting 17 with, for example, hydroxylamine hydrochloride or methoxylamine hydrochloride in the presence of a suitable base, such as pyridine, and in an appropriate solvent, for instance methanol, at ambient temperature. Imines 20 are synthesized by treating 17 with primary amines, as described in March, J. "Advanced Organic Chemistry", 4th ed.; John Wiley & Sons: New York, 1992; p 896–897. Olefinic derivatives 21 are prepared by reacting 17 with various olefinating reagents, such as phosphorus ylides and the like, which are known to one skilled in the art. Representative examples are described in March, J. "Advanced Organic Chemistry", 4th ed.; John Wiley & Sons: New York, 1992; p 956–963. The ketone moiety of 17 is amenable to further modification. Reaction of 17 with Lawesson's reagent or alternative reagents, as described in March, J. "Advanced Organic Chemistry", 4th ed.; John Wiley & Sons: New York, 1992; p 893–894, provides the corresponding thioketone 22. It will be apparent to one skilled in the art that further transformations of 17–22 are possible. For example, catalytic hydrogenation conditions or borane-based reduction methods selectively reduce the ketone, oxime and olefin moieties, respectively, of 17, 19 and 21 to give the corresponding hydroxy, amino and alkyl derivatives, respectively. Compound 17 can also be converted to corresponding cyclic and acyclic ketals and dithio ketals by reacting 17 with diols, dithiols, alcohols or thiols under conditions, for example, described in Greene, T. W.; Wuts, P. G. M. "Protective Groups in Organic Synthesis", 2nd ed.; John Wiley & Sons: New York, 1991, p 177–207. Compounds 17–22 and the above described derivatives represent examples of fused bicyclic carbazine oxazolidinone antibacterial agents, which are the subject of this invention.

It will be apparent to those skilled in the art that the described synthetic procedures for making fused bicyclic diazinyl and carbazinyl oxazolidinone antibacterial agents are merely representative in nature and that alternative synthetic processes are known, for example some of those described in the cited references. It will also be apparent to those skilled in the art that the outlined synthetic process, with non-essential variations, is readily adaptable to the preparation of spirocyclic diazinyl and carbazinyl oxazolidinone antibacterial agents of structural Formula II, which are also the subject of this invention (see Chart VI).

EXAMPLE 1

(S)-N-[[3-[4-[cis-3-(carbobenzyloxy)-3,7-diazabicyclo[3.3.0]octan-7-yl]-3-fluorophenyl]-2-oxo-5-oxazolidinyl]methyl]acetamide Step 1: cis-3-benzyl-7-(2-fluoro-4-nitrophenyl)-3,7-diazabicyclo[3,3,0]octane To a solution of cis-3-benzyl-3,7-diazabicyclo[3.3.0] octane (0.35 g, 1.73 mmol) in acetonitrile (10 mL) is added 3,4-difluoronitrobenzene (0. 19 mL, 1. 73 mmol) and potassium carbonate (0.60 g, 4.33 mmol) under a nitrogen atmosphere at ambient temperature. The reaction is stirred 15 hours, concentrated in vacuo, and diluted with ethyl acetate (100 mL). The organic phase is washed with water (3×20 mL) and saline (20 mL), dried over sodium sulfate, concentrated in vacuo, and chromatographed on silica gel (230–400 mesh, 100 mL), eluting with chloroform/methanol (99/1). The appropriate fractions are combined ($R_f$=0.49, TLC, chloroform/methanol, 95/5) and concentrated in vacuo to give the title compound, NMR (CDCl$_3$) 7.94, 7.88, 7.29, 6.62, 3.73, 3.64, 3.44, 2.97, 2.75, 2.55.

Step 2: cis-3-(carbobenzyloxy)-7-[4-[(carbobenzyloxy) amino]-2-fluorophenyl]-3,7-diazabicyclo[3.3.0]octane cis-3-Benzyl-7-(2-fluoro-4-nitrophenyl)-3,7-diazabicyclo [3.3.0]octane (9.11 g, 26.71 mmol), THF (100 mL), and methanol (50 mL) are combined with 10% palladium on carbon (6.67 g) and ammonium formate (16.83 g, 266.90 mmol) under nitrogen, heated to reflux for 2.5 hours, cooled to ambient temperature, stirred 15 hours, filtered through celite and concentrated in vacuo to give crude cis-3-(4-amino-2-fluorophenyl)-3,7-diazabicyclo[3.3.0]octane. cis-3-(4-Amino-2-fluorophenyl)-3,7-diazabicyclo[3.3.0]octane, water (100 mL), acetone (100 mL), and potassium carbonate (7.75 g, 56.07 mmol) are combined, cooled to 0° C., and benzyl chloroformate is added slowly. The reaction is warmed to ambient temperature, stirred 15 hours, concentrated in vacuo, and diluted with ethyl acetate. The organic phase is washed with water (2×150 mL) and saline (150 mL), dried over sodium sulfate, concentrated in vacuo, and chromatographed on silica gel (230–400 mesh, 100 mL), eluting with hexane/ethyl acetate (80/20). The appropriate fractions are combined ($R_f$=0.41, TLC, hexane/ethyl acetate, 50/50) and concentrated in vacuo to give the title compound, mp 121–122° C.

Step 3: (R)-[3-[4-[cis-3-(carbobenzyloxy)-3,7-diazabicyclo [3.3.0]octan-7-yl]-3-fluorophenyl]-2-oxo-5-oxazolidinyl] methanol To a flame dried flask cooled to −78° C. and equipped with a nitrogen inlet is introduced cis-3-(carbobenzyloxy)-7-[4-[(carbobenzyloxy)amino]-2-fluorophenyl]-3,7-diazabicyclo[3.3.0]octane (7.25 g, 14.81 mmol), THF (100 mL), and 1.6 M butyl lithium (9.72 mL, 15.55 mmol). The reaction is stirred at −78° C. for 1 hour before (R)-(−)-glycidyl butyrate (2.26 mL, 15.99 mmol) is added slowly and stirred for 2 hours at −78° C. and 15 hours at ambient temperature. Saturated ammonium chloride (50 mL) is added and the aqueous phase is extracted with ethyl acetate (2×50 mL). The extracts are combined, washed with saline (50 mL), dried over sodium sulfate, concentrated in vacuo, and chromatographed on silica gel (230–400 mesh, 100 mL), eluting with chloroform/methanol (99/1). The appropriate fractions are combined ($R_f$=0.13, TLC, chloroform/methanol, 95/5) and concentrated in vacuo to give the title compound, mp 168–171° C.

Step 4: (S)-N-[[3-[4-[cis-3-(Carbobenzyloxy)-3,7-diazabicyclo[3.3.0]octan-7-yl]-3-fluorophenyl]-2-oxo-5-oxazolidinyl]methyl]acetamide To a flame dried flask equipped with a nitrogen inlet is introduced (R)-[3-[4-[cis-3-(carbobenzyloxy)-3,7-diazabicyclo[3.3.0]octan-7-yl]-3-fluorophenyl]-2-oxo-5-oxazolidinyl]methanol (1.75 g, 3.84 mmol) and methylene chloride (100 mL) cooled to 0° C. Triethylamine (0.80 mL, 5.76 mmol) and methanesulfonyl chloride are added, stirred at 0° C. for 2 hours, and warmed to ambient temperature for 1 hour. The reaction is washed with water (30 mL), saturated sodium bicarbonate (30 mL), and saline (30 mL), dried over sodium sulfate, and concentrated in vacuo to give the crude (R)-[[3-[4-[cis-3-(carbobenzyloxy)-3,7-diazabicyclo[3.3.0] octan-7-yl]-3-fluorophenyl]-2-oxo-5-oxazolidinyl]methyl] methanesulfonate. (R)-[[3-[4-[cis-3-(Carbobenzyloxy)-3,7-diazabicyclo[3.3.0]octan-7-yl]-3-fluorophenyl]-2-oxo-5-oxazolidinyl]methyl]methanesulfonate is combined in a resealable tube with THF (5 mL), isopropanol (5 mL), and concentrated ammonium hydroxide (10 mL) and heated to 95° C. for 10 hours. The reaction is diluted with methylene chloride (50 mL) and washed with saline (30 mL), dried over sodium sulfate, concentrated in vacuo to give (S)-[[3-[4-[cis-3-(carbobenzyloxy)-3,7-diazabicyclo[3.3.0]octan-7-yl]-3-fluorophenyl]-2-oxo-5-oxazolidinyl]methyl]amine. The crude (S)-[[3-[4-[cis-3-(carbobenzyloxy)-3,7-diazabicyclo[3.3.0]octan-7-yl]-3-fluorophenyl]-2-oxo-5-oxazolidinyl]methyl]amine (1.67 g, 3.67 mmol) is dissolved in methylene chloride (20 mL), cooled to 0° C. under nitrogen, pyridine (0.89 mL, 11.02 mmol) and acetic anhydride (0.43 mL, 4.59 mmol) are added, and the reaction is stirred 15 hours at ambient temperature. The reaction is diluted with methylene chloride (50 mL), washed with 1N HCl (25 mL), saturated sodium bicarbonate (25 mL), saline (25 mL), dried over sodium sulfate, concentrated in vacuo, and chromatographed on silica gel (230–400 mesh, 200 mL), eluting with chloroform/methanol (98/2). The appropriate fractions are combined ($R_f$=0.15, TLC, chloroform/methanol, 95/5) and concentrated in vacuo to give the title compound, mp 165–168° C.

EXAMPLE 2

(S)-N-[[3-[3-fluoro4-[cis-3-(benzyloxyacetyl)-3,7-diazabicyclo[3.3.0]octan-7-yl]phenyl]-2-oxo-5-oxazolidinyl]methyl]acetamide (S)-N-[[3-[4-[cis-3-(Carbobenzyloxy)-3,7-ciazabicyclo [3.3.0]octan-7-yl]-3-fluorophenyl]-2-oxo-5-oxazolidinyl]

methyl]acetamide (150 mg, 0.30 mmol), methylene chloride (5 mL), and methanol (10 mL) are combined with 10% palladium on carbon (30 mg) and placed under a hydrogen atmosphere (balloon) for 15 hours. The reaction is filtered through celite and concentrated in vacuo to give crude (S)-N-[[3-[4-[cis-3,7-diazabicyclo[3.3.0]octan-7-yl]-3-fluorophenyl]-2-oxo-5-oxazolidinyl]methyl]acetamide. The crude amine is taken up in methylene chloride (15 mL), cooled to 0° C., and triethylamine (0.09 mL, 0.67 mmol) and benzyloxyacetyl chloride (0.06 mL, 0.40 mmol) are added. The reaction is warmed to ambient temperature, stirred 15 hours, and diluted with methylene chloride (100 mL). The organic phase is washed with water (2×50 mL) and saline (150 mL), dried over sodium sulfate, concentrated in vacuo, and chromatographed on silica gel (230–400 mesh, 100 mL), eluting with chloroform/methanol (95/5). The appropriate fractions are combined ($R_f$=0.41, TLC, chloroform/methanol, 90/10) and concentrated in vacuo to give the title compound, mp 138–140° C.

EXAMPLE 3

(S)-N-[[3-[3-fluoro4-[cis-3-(hydroxyacetyl)-3,7-diazabicyclo[3.3.0]octan-7-yl]phenyl]-2-oxo-5-oxazolidinyl]methyl]acetamide The (S)-N-[[3-[3-fluoro-4-[cis-3-(benzyloxyacetyl)-3,7-diazabicyclo[3.3.0]octan- 7-yl]phenyl]-2-oxo-5-oxazolidinyl]methyl]acetamide (110 mg, 0.22 mmol), methanol (25 mL) and 10% palladium on carbon (100 mg) are combined and placed under 40 p.s.i. of hydrogen and shaken for 5 days. The reaction is filtered through celite, concentrated in vacuo, and chromatographed on silica gel (230–400 mesh, 100 mL), eluting with chloroform/methanol (95/5). The appropriate fractions are combined ($R_f$=0.20, TLC, chloroform/methanol, 90/10) and concentrated in vacuo to give the title compound, mp 167–168° C.

EXAMPLE 4

(S)-N-[[3-[3-fluoro-4-[cis-3-(5-isoxazolinoyl)-3,7-diazabicyclo[3.3.0]octan-7-yl]phenyl]-2-oxo-5-oxazolidinyl]methyl]acetamide (S)-N-[[3-[4-[cis-3-(Carbobenzyloxy)-3,7-diazabicyclo[3.3.0]octan-7-yl]-3-fluorophenyl]-2-oxo-5-oxazolidinyl]methyl]acetamide (150 mg, 0.30 mmol), methylene chloride (5 mL), and methanol (10 mL) are combined with 10% palladium on carbon (30 mg) and placed under a hydrogen atmosphere (balloon) for 15 hours. The reaction is filtered through celite and concentrated in vacuo to give crude (S)-N-[[3-[4-[cis- 3,7-diazabicyclo[3.3.0]octan-7-yl]-3-fluorophenyl]-2-oxo-5-oxazolidinyl]methyl]acetamide. To the crude (S)-N-[[3-[4-[cis-3,7-diazabicyclo[3.3.0]octan-7-yl]-3-fluorophenyl]-2-oxo-5-oxazolidinyl]methyl]acetamide (115 mg, 0.30 mmol) dissolved in pyridine (5 mL) at 0° C. is added 1-(3-dimethylaminopropyl)-3-ethylcarbodiimide hydrochloride (70 mg, 0.35 mmol), 4-dimethylaminopyridine (5 mg, 0.05 mmol), and isoxazole-5-carboxylic acid (40 mg, 0.35 mmol). The reaction is warmed to ambient temperature, stirred 15 hours, diluted with methylene chloride (30 mL). The organic phase is washed with 1N HCl (20 mL) and saline (20 mL), dried over sodium sulfate, concentrated in vacuo, and chromatographed on silica gel (230–400 mesh, 100 mL), eluting with chloroform/methanol (97/3). The appropriate fractions are combined ($R_f$=0.16, TLC, chloroform/methanol, 95/5) and concentrated in vacuo to give the title compound, mp 172–175° C.

EXAMPLE 5

(S)-N-[[3-[3-fluoro-4-[cis-3-(2-indolylcarbonyl)-3,7-diazabicyclo[3.3.0]octan-7-yl]phenyl]-2-oxo-5-oxazolidinyl]methyl]acetamide Following the general procedure of EXAMPLE 4 and making noncritical variations but substituting indole-2-carboxylic acid (60 mg, 0.35 mmol) for isoxazole-5-carboxylic acid, the title compound is obtained, mp 211° C.

EXAMPLE 6

(s)-N-[[3-[3-fluoro-4-[cis-3-(carbomethoxy)-3,7-diazabicyclo[3.3.0]octan- 7-yl]phenyl]-2-oxo-5-oxazolidinyl]methyl]acetamide Following the general procedure of EXAMPLE 2 and making noncritical variations but substituting methyl chloroformate (80 mg, 0.80 mmol) for benzyloxyacetyl chloride, sodium bicarbonate (240 mg, 2.80 mmol) for triethylamine, and using acetone (5 mL) and water (5 mL) as solvent, the title compound is obtained, mp 128–132° C.

EXAMPLE 7

(S)-N-[[3-[3-fluoro-4-[cis-3-(formyl)-3,7-diazabicyclo[3.3.0]octan-7-yl]phenyl]-2-oxo-5-oxazolidinyl]methyl]acetamide Following the general procedure of EXAMPLE 4 and making noncritical variations but substituting formic acid (40 mg, 0.60 mmol) for isoxazole-5-carboxylic acid, the title compound is obtained, HRMS calcd for $C_{19}H_{23}N_4FO_4$: 390.1703. Found: 390.1709.

EXAMPLE 8

(S)-N-[[3-[3-fluoro-4-[cis-3-(acetyl)-3,7-diazabicyclo[3.3.0]octan-7-yl]phenyl]-2-oxo-5-oxazolidinyl]methyl]acetamide Following the general procedure of EXAMPLE 2 and making noncritical variations but substituting acetyl chloride (80 mg, 1.05 mmol) for benzyloxyacetyl chloride, the title compound is obtained, mp 168–170° C.

EXAMPLE 9

(S)-N-[[3-[4-[cis-3-(carbobenzyloxy)-3,7-diazabicyclo[3.3.0]octan-7-yl]phenyl]-2-oxo-5-oxazolidinyl]methyl]acetamide Step 1: cis-3-benzyl-7-(4-nitrophenyl)-3,7-diazabicyclo [3.3.0]octane Following the general procedure of EXAMPLE 1, Step 1 and making noncritical variations but substituting 4-fluoronitrobenzene (8.16 g, 57.80 mmol) for 3,4-difluoronitrobenzene, the intermediate title compound is obtained, mp 121–123° C.

Step 2: cis-3-(carbobenzyloxy)-7-[4-[(carbobenzyloxy) amino]phenyl]-3,7-diazabicyclo[3.3.0]octane Following the general procedure of EXAMPLE 1, Step 2 and making noncritical variations but substituting cis-3-benzyl-7-(4-nitrophenyl)-3,7-diazabicyclo[3.3.0]octane (1.00 g, 3.10 mmol) for cis-3-benzyl-7-(2-fluoro-4-nitrophenyl)-3,7-diazabicyclo[3.3.0]octane, the intermediate title compound is obtained, mp 145–146° C.

Step 3: (R)-[3-[4-[cis-3-(carbobenzyloxy)-3,7-diazabicyclo [3.3.0]octan-7-yl]phenyl]-2-oxo-5-oxazolidinyl]methanol Following the general procedure of EXAMPLE 1, Step 3 and making noncritical variations but substituting cis-3-

(carbobenzyloxy)-7-[4-[(carbobenzyloxy)amino]phenyl]-3,7-diazabicyclo[3.3.0]octane (575 mg, 1.22 mmol) for cis-3-(carbobenzyloxy)-7-[4-[(carbobenzyloxy)amino]-3-fluorophenyl]-3,7-diazabicyclo[3.3.0]octane, the intermediate title compound is obtained, mp 163–164° C.

Step 4: (S)-N-[[3-[4-[cis-3-(carbobenzyloxy)-3,7-diazabicyclo[3.3.0]octan-7-yl]phenyl]-2-oxo-5-oxazolidinyl]methyl]acetamide Following the general procedure of EXAMPLE 1, Step 4 and making noncritical variations but substituting (R)-[3-[4-[cis-3-(carbobenzyloxy)-3,7-diazabicyclo[3.3.0]octan-7-yl]phenyl]-2-oxo-5-oxazolidinyl]methanol (280 mg, 0.65 mmol) for (R)-[[3-[4-[cis-3-(carbobenzyloxy)-3,7-diazabicyclo[3.3.0]octan-7-yl]-3-fluorophenyl]-2-oxo-5-oxazolidinyl]methanol, the title compound is obtained, mp 135–140° C.

EXAMPLE 10

(S)-N-[[3-[3-fluoro-4-[cis-2-(carbobenzyloxy)-2,8-diazabicyclo[4.3.0]nonan-8-yl]phenyl]-2-oxo-5-oxazolidinyl]methyl]acetamide Step 1:

(±)-cis-2,8-diazabicyclo[4.3.0]nonane (24.6 mmol) was dissolved into 30 mL of dry DMSO. The solution was treated with $K_2HPO_4$ (8.6 g, 49.2 mmol) followed by 3,4-difluoronitrobenzene (3.9 g, 24.6 mmol). The mixture became a bright orange color. The mixture was stirred for 20 hours at ambient temperature under $N_2$. After this time the mixture was poured into a separatory funnel along with $CHCl_3$. The solution was washed with $H_2O$ and brine. The organic phase was separated and dried over anhydrous $Na_2SO_4$. The solution was filtered and concentrated to give an orange oil that was purified by chromatography on silica gel eluting with a gradient of 1–5% $MeOH/CHCl_3$. This gave 4.2 g of product as an orange waxy solid. MP: 77–79° C.

Step 2:

The nitro aromatic product obtained in Step 1 (1.5 g, 5.65 mmol) was dissolved into 50 mL of THF. The solution was treated with the catalyst 10% Pd/C under a stream of $N_2$. The mixture was degassed by evacuation and flushing with $N_2$ (3 times), followed by evacuation and flush with $H_2$ (3 times). The mixture was maintained at 35 psi of $H_2$ and was shaken on the parr. After 4 hours of reaction time TLC showed starting material was consumed. This solution was diluted with 50 mL of 1:1 acetone/$H_2O$ and the mixture was cooled to 0° C. The reaction mixture was treated with solid $NaHCO_3$ (1.4 g, 17.0 mmol) followed by benzyl chloroformate (2.0 g, 11.9 inmol). This mixture was left to stir overnight with warming to room temperature. After 16 hours the reaction mixture was diluted with $CH_2Cl_2$ and filtered through celite. The filtrate was poured into a separatory funnel along with $H_2O$. The mixture was shaken and the organic phase was separated, washed with brine followed by drying over anhydrous $Na_2SO_4$. The solution was filtered and concentrated to give a solid that was purified by chromatography on silica gel eluting with 5:1 hexane/EtOAc. Isolated 2.0 g of U-141248 as a yellow solid. This material was recystallyzed from 10% EtOAc/hexane to give a white solid. MP: 139–140° C.

Step 3:

The product of Step 2 (505 mg, 1.00 mmol) was dissolved into 10 mL of dry THF and the solution was cooled to −78° C. The solution was treated with n-BuLi (1.6 M soln. in hexanes; Aldrich; 656 μL, 1.05 mmol) via syringe. After 10 minutes (R)-glycidyl butyrate (151 mg, 1.05 mmol) was added and the mixture was left to stir overnight with warming to room temperature. After 14 hours the mixture was examined by TLC which showed the starting material was consumed. The reaction was poured into a separatory funnel along with EtOAc. The mixture was washed with saturated aqueous $NH_4Cl$ and brine. The organic phase was separated and dried over anhydrous $Na_2SO_4$. Filtered and concentrated to give a residue that was purified by radial chromatography eluting with a gradient of 1–3% MeOH/$CHCl_3$. Isolated 294 mg of 5-(hydroxymethyl) oxazolidinone intermediate as a tan foam. MP: 71–73° C.

Step 4:

The alcohol obtained in Step3 (880 mg, 1.90 mmol) was dissolved into 15 mL of dry $CH_2Cl_2$ and the solution was cooled to 0° C. The solution was treated with $Et_3N$ (336 mg, 3.32 mmol) and stirred for 5 minutes. Next solid 3-nitrobenzenesulfonyl chloride (NosylCl, 561 mg, 2.53 mmol) was added and the mixture was stored in the freezer overnight. After 15 hours TLC showed the starting alcohol was consumed with the formation of a new higher $R_f$ product. The reaction was poured into a separatory funnel along with $CH_2Cl_2$. The solution was washed with 1.0 N aqueous HCl and saturated sodium bicarbonate. The organic phase was separated and dried over anhydrous $Na_2SO_4$. Filtered and concentrated to give 1.3 g of the nosylate as an orange foam. This material was used without purification.

Step 5:

The crude nosylate (1.9 mmol) was dissolved into 10 mL of $CH_3CN$ and the solution was transfered to a resealable tube. The solution was diluted with 5 mL of isopropanol and 10 mL of 28% aqueous $NH_4OH$. The tube was sealed and heated to 65° C. After 15 hours the solution was cooled to ambient temperature and TLC showed that the nosylate was consumed. The reaction was poured into a separatory funnel along with $CH_2Cl_2$. The solution was washed with saturated aqueous $NaHCO_3$ and brine. The organic phase was separated and dried over anhydrous $Na_2SO_4$. Filtered and concentrated to give the crude amine as a foam. This material was dissolved into 20 mL of dry $CH_2Cl_2$ and the solution was cooled to 0° C. The reaction was treated with 500 μL of dry pyridine along with an excess of $Ac_2O$ (200 μL). This mixture was left to stir overnight with warming to room temperature. After 18 hours the reaction mixture was poured into a separatory funnel along with $CH_2Cl_2$. The solution was washed with 1.0 N aqueous HCl and saturated aqueous $NaHCO_3$. The organic phase was separated and dried over anhydrous $Na_2SO_4$. The solution was filtered and concentrated to give a tan foam that was purified on silica gel by radial chromatography eluting with 3% MeOH/$CHCl_3$. This provided 776 mg of the title compound as a tan foam (mixture of diastereomers). MP: 74–76° C. HRMS (EI) calcd for $C_{27}H_{31}FN_4O_5$ 510.2278, found 510.2278.

EXAMPLE 11

(S)-N-[[3-[3-fluoro-4-[cis-2-(carbomethoxy)-2,8-diazabicyclo[4.3.0]nonan-8-yl]phenyl]-2-oxo-5-oxazolidiny]methyl]acetamide Step 1:

The starting material, EXAMPLE 10, (850 mg, 1.7 mmol) was dissolved into 20 mL of MeOH. The solution was treated with the catalyst 10% Pd/C (85 mg) under a stream of $N_2$. The parr bottle was evacuated and flushed with $N_2$ (3 times) followed by evacuation and flushed with $H_2$ (3 times). The mixture was maintained at 35 psi of $H_2$ pressure and was shaken on the parr. After 10 hours of reaction time TLC showed starting material was consumed. The solution was filtered through celite and the filtrate was concentrated under reduced pressure to give 585 mg of a tan foam. This crude amine was used without purification.

Step 2:

The crude amine (380 mg, 1.01 mmol) was dissolved into 2:1 acetone/H$_2$O and the solution was cooled to 0° C. Solid NaHCO$_3$ (170 mg, 2.02 mmol) was added along with methyl chloroformate (119 mg, 1.26 mmol). The mixture was left to stir overnight with warming to room temperature. After 16 hours the reaction mixture was poured into a separatory funnel along with CH$_2$Cl$_2$. The mixture was washed with H$_2$O and brine. The organic phase was separated and dried over anhydrous Na$_2$SO$_4$. The solution was filtered and concentrated to give a white foam that was purified by radial chromatography eluting with 20% CH$_3$CN/CHCl$_3$. This gave 367 mg of the title compound as a white foam (mixture of diastereomers). MP: 83–85° C.

HRMS (EI) calcd for C$_{21}$H$_{27}$FN$_4$O$_5$ 434.1965, found 434.1971.

EXAMPLE 12

(S)-N-[[3-[3-fluoro-4-[cis-2-(acetoxyacetyl)-2,8-diazabicyclo[4.3.0]nonan-8-yl]phenyl]-2-oxo-5-oxazolidinyl]methyl]acetamide Step 1:

The crude amine intermediate described in EXAMPLE 11, Step 1, (500 mg, 1.33 mmol) was dissolved into 10 mL of dry CH$_2$Cl$_2$. The solution was cooled to 0° C. and treated with 1.0 mL of dry pyridine followed by acetoxyacetyl chloride (218 mg, 1.59 mmol). This mixture was left to stir overnight with warming to room temperature. After 18 hours TLC showed starting material was consumed. The reaction mixture was poured into a separatory funnel along with CH$_2$Cl$_2$. The solution was washed with 0.5 N aqueous HCl, saturated aqueous NaHCO$_3$ and brine. The organic phase was separated and dried over anhydrous Na$_2$SO$_4$. Filtered and concentrated to give a gum that was purified by radial chromatography eluting with 10% CH$_3$CN/2% MeOH/CHCl$_3$. This gave 426 mg of the title compound as a white foamy solid (mixture of diastereomers). MP: 113–116° C. HRMS (EI) calcd for C$_{23}$H$_{29}$FN$_4$O$_6$ 476.2071, found 476.2065.

EXAMPLE 13

(S)-N-[[3-[3-fluoro-4-[cis-2-(hydroxyacetyl)-2,8-diazabicyclo[4.3.0]nonan-8-yl]phenyl]-2-oxo-5-oxazolidinyl]methyl]acetamide Step 1:

The starting material, EXAMPLE 12, (325 mg, 0.68 mmol) was dissolved into 6 mL of MeOH. The solution was cooled to 0° C. under N$_2$. The solution was treated with 3.0 mL of 10% aqueous K$_2$CO$_3$. The mixture was stirred for 2 hours. After this time TLC showed U-141950 was consumed. The reaction was quenched with 1.0 N aqueous HCl to pH 6.5 (litmus). The reaction mixture was poured into a separatory funnel along with CH$_2$Cl$_2$. The solution was washed with H$_2$O and brine. The organic phase was separated and dried over anhydrous Na$_2$SO$_4$. Filtered and concentrated to give 276 mg of the title compound as a white foam (mixture of diastereomers). MP: 102–110° C. HRMS (EI) calcd for C$_{21}$H$_{27}$FN$_4$O$_5$ 434.1965, found 434.1975.

Following the general procedures outlined in the Charts and in view of the techniques used in the Examples 1–13, in particular to prepare (S)-N-[[3-[3-fluoro-4-[cis-3-(carbobenzyloxy)-3,7-diazabicyclo[3.3.0]octan-7-yl]phenyl]-2-oxo-5-oxazolidinyl]methyl]acetamide (Example 1), (S)-N-[[3-[3-fluoro-4-[cis-3-(benzyloxyacetyl)-3,7-diazabicyclo[3.3.0]octan-7-yl]phenyl]-2-oxo-5-oxazolidinyl]methyl]acetamide (Example 2); (S)-N-[[3-[3-fluoro-4-[cis-3-(hydroxyacetyl)-3,7-diazabicyclo[3.3.0]octan-7-yl]phenyl]-2-oxo-5-oxazolidinyl]methyl]acetamide (Example 3); and (S)-N-[[3-[3-fluoro4-[cis-3-(5-isoxazolinoyl)-3,7-diazabicyclo[3.3.0]octan-7-yl]phenyl]-2-oxo-5-oxazolidinyl]methyl]acetamide (Example 4) the following additional compounds of Formula I can be prepared:

(S)-N-[[3-[3-fluoro-4-[cis-3-(acetoxyacetyl)-3,7-diazabicyclo[3.3.0]octan-7-yl]phenyl]-2-oxo-5-oxazolidinyl]methyl]acetamide;

(S)-N-[[3-[3-fluoro4-[cis-3-(formyl)-3,7-diazabicyclo[3.3.0]octan-7-yl]phenyl]-2-oxo-5-oxazolidinyl]methyl]acetamide;

(S)-N-[[3-[3-fluoro4-[cis-3-(methylsulfonyl)-3,7-diazabicyclo[3.3.0]octan-7-yl]phenyl]-2-oxo-5-oxazolidinyl]methyl]acetamide;

(S)-N-[[3-[3-fluoro4-[cis-3-(2-fluoroethyl)-3,7-diazabicyclo[3.3.0]octan-7-yl]phenyl]-2-oxo-5-oxazolidinyl]methyl]acetamide; (S)-N-[[3-[3-fluoro-4-[cis-3-(2-hydroxyethyl)-3,7-diazabicyclo[3.3.0]octan-7-yl]phenyl]-2-oxo-5-oxazolidinyl]methyl]acetamide; (S)-N-[[3-[3-fluoro-4-[cis-3-(2-methoxyethyl)-3,7-diazabicyclo[3.3.0]octan-7-yl]phenyl]-2-oxo-5-oxazolidinyl]methyl]acetamide; (S)-N-[[3-[3-fluoro4-[cis-3-(cyanomethyl)-3,7-diazabicyclo[3.3.0]octan-7-yl]phenyl]-2-oxo-5-oxazolidinyl]methyl]acetamide;

(S)-N-[[3-[3-fluoro4-[cis-3-(carbomethoxy)-3,7-diazabicyclo[3.3.0]octan-7-yl]phenyl]-2-oxo-5-oxazolidinyl]methyl]acetamide;

(S)-N-[[3-[3-fluoro4-[(S,S)-2-(carbobenzyloxy)-2,8-diazabicyclo[4.3.0]non-8-yl]phenyl]-2-oxo-5-oxazolidinyl]methyl]acetamide;

(S)-N-[[3-[3-fluoro4-[(S,S)-2-(hydroxyacetyl)-2,8-diazabicyclo[4.3.0]non-8-yl]phenyl]-2-oxo-5-oxazolidinyl]methyl]acetamide;

(S)-N-[[3-[3-fluoro4-[(SS)-2-(acetoxyacetyl)-2,8-diazabicyclo[4.3.0]non-8-yl]phenyl]-2-oxo-5-oxazolidinyl]methyl]acetamide;

(S)-N-[[3-[3-fluoro-4-[(S,S)-2-(formyl)-2,8-diazabicyclo[4.3.0]non-8-yl]phenyl]-2-oxo-5-oxazolidinyl]methyl]acetamide;

(S)-N-[[3-[3-fluoro4-[(S,S)-2-(methylsulfonyl)-2,8-diazabicyclo[4.3.0]non-8-yl]phenyl]-2-oxo-5-oxazolidinyl]methyl]acetamide;

(S)-N-[[3-[3-fluoro4-[(S,S)-2-(2-fluoroethyl)-2,8-diazabicyclo[4.3.0]non-8-yl]phenyl]-2-oxo-5-oxazolidinyl]methyl]acetamide;

(S)-N-[[3-[3-fluoro4-[(S,S)-2-(2-hydroxyethyl)-2,8-diazabicyclo[4.3.0]non-8-yl]phenyl]-2-oxo-5-oxazolidinyl]methyl]acetamide;

(S)-N-[[3-[3-fluoro4-[(S,S)-2-(2-methoxyethyl)-2,8-diazabicyclo[4.3.0]non-8-yl]phenyl]-2-oxo-5-oxazolidinyl]methyl]acetamide;

(S)-N-[[3-[3-fluoro-4-[(S,S)-2-(cyanomethyl)-2,8-diazabicyclo[4.3.0]non-8-yl]phenyl]-2-oxo-5-oxazolidinyl]methyl]acetamide;

(S)-N-[[3-[3-fluoro-4-[(S,S)-2-(carbomethoxy)-2,8-diazabicyclo[4.3.0]non-8-yl]phenyl]-2-oxo-5-oxazolidinyl]methyl]acetamide;

(S)-N-[[3-[3-fluoro4-[(R,R)-2-(carbobenzyloxy)-2,8-diazabicyclo[4.3.0]non-8-yl]phenyl]-2-oxo-5-oxazolidinyl]methyl]acetamide;

(S)-N-[[3-[3-fluoro-4-[(R,R)-2-(hydroxyacetyl)-2,8-diazabicyclo[4.3.0]non-8-yl]phenyl]-2-oxo-5-oxazolidinyl]methyl]acetamide;

(S)-N-[[3-[3-fluoro-4-[(R,R)-2-(acetoxyacetyl)-2,8-diazabicyclo[4.3.0]non-8-yl]phenyl]-2-oxo-5-oxazolidinyl]methyl]acetamide;

(S)-N-[[3-[3-fluoro4-[(R,R)-2-(formyl)-2,8-diazabicyclo[4.3.0]non-8-yl]phenyl)-2-oxo-5-oxazolidinyl]methyl]acetamide;

(S)-N-[[3-[3-fluoro-4-[(R,R)-2-(methylsulfonyl)-2,8-diazabicyclo[4.3.0]non-8-yl]phenyl]-2-oxo-5-oxazolidinyl]methyl]acetamide;

(S)-N-[[3-[3-fluoro4-[(R,R)-2-(2-fluoroethyl)-2,8-diazabicyclo[4.3.0]non-8-yl]phenyl]-2-oxo-5-oxazolidinyl]methyl]acetamide;

(S)-N-[[3-[3-fluoro-4-[(R,R)-2-(2-hydroxyethyl)-2,8-diazabicyclo[4.3.0]non-8-yl]phenyl]-2-oxo-5-oxazolidinyl]methyl]acetamide;

(S)-N-[[3-[3-fluoro-4-[(R,R)-2-(2-methoxyethyl)-2,8-diazabicyclo[4.3.0]non-8-yl]phenyl]-2-oxo-5-oxazolidinyl]methyl]acetamide;

(S)-N-[[3-[3-fluoro-4-[(R,R)-2-(cyanomethyl)-2,8-diazabicyclo[4.3.0]non-8-yl]phenyl]-2-oxo-5-oxazolidinyl]methyl]acetamide;

(S)-N-[[3-[3-fluoro-4-[(R,R)-2-(carbomethoxy)-2,8-diazabicyclo[4.3.0]non-8-yl]phenyl]-2-oxo-5-oxazolidinyl]methyl]acetamide;

(S)-N-[[3-[3-fluoro-4-[cis-3-(carbobenzyloxy)-3,6-diazabicyclo[3.2.0]heptan-6-yl]phenyl]-2-oxo-5-oxazolidinyl]methyl]acetamide;

(S)-N-[[3-[3-fluoro-4-[cis-3-(hydroxyacetyl)-3,6-diazabicyclo[3.2.0]heptan-6-yl]phenyl]-2-oxo-5-oxazolidinyl]methyl]acetamide;

(S)-N-[[3-[3-fluoro-4-[cis-3-(acetoxyacetyl)-3,6-diazabicyclo[3.2.0]heptan-6-yl]phenyl]-2-oxo-5-oxazolidinyl]methyl]acetamide;

(S)-N-[[3-[3-fluoro-4-[cis-3-(formyl)-3,6-diazabicyclo[3.2.0]heptan-6-yl]phenyl]-2-oxo-5-oxazolidinyl]methyl]acetamide;

(S)-N-[[3-[3-fluoro4-[cis-3-(methylsulfonyl)-3,6-diazabicyclo[3.2.0]heptan-6-yl]phenyl]-2-oxo-5-oxazolidinyl]methyl]acetamide;

(S)-N-[[3-[3-fluoro-4-[cis-3-(2-fluoroethyl)-3,6-diazabicyclo[3.2.0]heptan-6-yl]phenyl]-2-oxo-5-oxazolidinyl]methyl]acetamide;

(S)-N-[[3-[3-fluoro4-[cis-3-(2-hydroxyethyl)-3,6-diazabicyclo[3.2.0]heptan-6-yl]phenyl]-2-oxo-5-oxazolidinyl]methyl]acetamide;

(S)-N-[[3-[3-fluoro-4-[cis-3-(2-methoxyethyl)-3,6-diazabicyclo[3.2.0]heptan-6-yl]phenyl]-2-oxo-5-oxazolidinyl]methyl]acetamide;

(S)-N-[[3-[3-fluoro-4-[cis-3-(cyanomethyl)-3,6-diazabicyclo[3.2.0]heptan-6-yl]phenyl]-2-oxo-5-oxazolidinyl]methyl]acetamide;

(S)-N-[[3-[3-fluoro-4-[cis-3-(carbomethoxy)-3,6-diazabicyclo[3.2.0]heptan-6-yl]phenyl]-2-oxo-5-oxazolidinyl]methyl]acetamide;

(S)-N-[[3-[3-fluoro-4-[cis-6-(carbobenzyloxy)-3,6-diazabicyclo[3.2.0]heptan-3-yl]phenyl]-2-oxo-5-oxazolidinyl]methyl]acetamide;

(S)-N-[[3-[3-fluoro-4-[cis-6-(hydroxyacetyl)-3,6-diazabicyclo[3.2.0]heptan-3-yl]phenyl]-2-oxo-5-oxazolidinyl]methyl]acetamide;

(S)-N-[[3-[3-fluoro-4-[cis-6-(acetoxyacetyl)-3,6-diazabicyclo[3.2.0]heptan-3-yl]phenyl]-2-oxo-5-oxazolidinyl]methyl]acetamide;

(S)-N-[[3-[3-fluoro-4-[cis-6-(formyl)-3,6-diazabicyclo[3.2.0]heptan-3-yl]phenyl]-2-oxo-5-oxazolidinyl]methyl]acetamide;

(S)-N-[[3-[3-fluoro-4-[cis-6-(methylsulfonyl)-3,6-diazabicyclo[3.2.0]heptan-3-yl]phenyl]-2-oxo-5-oxazolidinyl]methyl]acetamide;

(S)-N-[[3-[3-fluoro-4-[cis-6-(2-fluoroethyl)-3,6-diazabicyclo[3.2.0]heptan-3-yl]phenyl]-2-oxo-5-oxazolidinyl]methyl]acetamide;

(S)-N-[[3-[3-fluoro4-[cis-6-(2-hydroxyethyl)-3,6-diazabicyclo[3.2.0]heptan-3-yl]phenyl]-2-oxo-5-oxazolidinyl]methyl]acetamide;

(S)-N-[[3-[3-fluoro-4-[cis-6-(2-methoxyethyl)-3,6-diazabicyclo[3.2.0]heptan-3-yl]phenyl]-2-oxo-5-oxazolidinyl]methyl]acetamide;

(S)-N-[[3-[3-fluoro4-[cis-6-(cyanomethyl)-3,6-diazabicyclo[3.2.0]heptan-3-yl]phenyl]-2-oxo-5-oxazolidinyl]methyl]acetarnide;

(S)-N-[[3-[3-fluoro-4-[cis-6-(carbomethoxy)-3,6-diazabicyclo[3.2.0]heptan-3-yl]phenyl]-2-oxo-5-oxazolidinyl]methyl]acetamide;

(S)-N-[[3-[3-fluoro4-[cis-3-aza-6-oxobicyclo[3.2.0]heptan-3-yl]phenyl]-2-oxo-5-oxazolidinyl]methyl]acetamide;

(S)-N-[[3-[3-fluoro-4-[cis-3-aza-6-(hydroxyirnino)bicyclo[3.2.0]heptan-3-yl]phenyl]-2-oxo-5-oxazolidinyl]methyl]acetamide;

(S)-N-[[3-[3-fluoro-4-[cis-3-aza-6-(methoxyimino)bicyclo[3.2.0]heptan-3-yl]phenyl]-2-oxo-5-oxazolidinyl]methyl]acetamide;

(S)-N-[[3-[3-fluoro-4-[cis-3-aza-6-oxobicyclo[3.2.0]heptan-3-yl]phenyl]-2-oxo-5-oxazolidinyl]methyl]acetamide ethylene ketal;

(S)-N-[[3-[3-fluoro-4-[trans-3-aza-7-oxobicyclo[4.4.0]decan-3-yl]phenyl]-2-oxo-5-oxazolidinyl]methyl]acetamide;

(S)-N-[[3-[3-fluoro-4-[trans-3-aza-7-(methoxyimino)bicyclo[4.4.0]decan-3-yl]phenyl]-2-oxo-5-oxazolidinyl]methyl]acetamide;

(S)-N-[[3-[3-fluoro-4-[trans-3-aza-7-(hydroxyimino)bicyclo[4.4.0]decan-3-yl]phenyl]-2-oxo-5-oxazolidinyl]methyl]acetamide;

(S)-N-[[3-[3-fluoro-4-[trans-3-aza-7-oxobicyclo[4.4.0]decan-3-yl]phenyl]-2-oxo-5-oxazolidinyl]methyl]acetamide ethylene ketal;

(S)-N-[[3-[3-fluoro-4-[cis-3-[2-(ethylsulfenyl)ethyl]-3,7-diazabicyc[3.3.0]octan-7-yl]phenyl]-2-oxo-5-oxazolidinyl]methyl]acetamide;

(S)-N-[[3-[3-fluoro-4-[cis-3-[2-[(4-morpholinyl)sulfonyl]ethyl]-3,7-diazabicyclo[3.3.0]octan-7-yl]phenyl]-2-oxo-5-oxazolidinyl]methyl]acetamide;

(S)-N-[[3-[3-fluoro-4-[(S,S)-2-[2-(ethylsulfenyl)ethyl]-2,8-diazabicyclo[4.3.0]non-8-yl]phenyl]-2-oxo-5-oxazolidinyl]methyl]acetamide;

(S)-N-[[3-[3-fluoro-4-[(S,S)-2-[2-[(4-morpholinyl)sulfonyl]ethyl]-2,8-diazabicyclo[4.3.0]non-8-yl]phenyl]-2-oxo-5-oxazolidinyl]methyl]acetamide;

(S)-N-[[3-[3-fluoro-4-[(R,R)-2-[(4-morpholinyl)sulfonyl]ethyl]-2,8-diazabicyclo[4.3.0]non-8-yl]phenyl]-2-oxo-5-oxazolidinyl]methyl]acetamide;

(S)-N-[[3-[3-fluoro-4-[(R,R)-2-[2-(ethylsulfenyl)ethyl]-2,8-diazabicyclo [4.3.0]non-8-yl]phenyl]-2-oxo-5-oxazolidinyl]methyl]acetamide;

(S)-N-[[3-[3-fluoro-4-[cis-3-(2-fluorobenzoyl)-3,7-diazabicyclo[3.3.0]octan-7-yl]phenyl]-2-oxo-5-oxazolidinyl]methyl]acetamide;

(S)-N-[[3-[3-fluoro-4-[cis-3-[(cyclopropyl)carbonyl]-3,7-diazabicyclo[3.3.0]octan-7-yl]phenyl]-2-oxo-5-oxazolidinyl]methyl]acetamide;

(S)-N-[[3-[3-fluoro-4-[(S,S)-2-(2-fluorobenzoyl)-2,8-diazabicyclo[4.3.0]non-8-yl]phenyl]-2-oxo-5-oxazolidinyl]methyl]acetamide;

(S)-N-[[3-[3-fluoro-4-[(S,S)-2-[(cyclopropyl)carbonyl]-2,8-diazabicyclo[4.3.0]non-8-yl]phenyl]-2-oxo-5-oxazolidinyl]methyl]acetamide;

(S)-N-[[3-[3-fluoro-4-[(R,R)-2-(2-fluorobenzoyl)-2,8-diazabicyclo[4.3.0]non-8-yl]phenyl]-2-oxo-5-oxazolidinyl]methyl]acetamide;

(S)-N-[[3-[3-fluoro-4-[(R,R)-2-[(cyclopropyl)carbonyl]-2,8-diazabicyclo[4.3.0]non-8-yl]phenyl]-2-oxo-5-oxazolidinyl]methyl]acetamide;

(S)-N-[[3-[3-fluoro-4-[cis-3-(methoxyacetyl)-3,7-diazabicyclo[3.3.0]octan-7-yl]phenyl]-2-oxo-5-oxazolidinyl]methyl]acetamide;

(S)-N-[[3-[3-fluoro-4-[cis-3-(methoxyacetyl)-3,7-diazabicyclo[3.3.0]octan-7-yl]phenyl]-2-oxo-5-oxazolidinyl]methyl]acetamide;

(S)-N-[[3-[3-fluoro-4-[(S,S)-2-(methoxyacetyl)-2,8-diazabicyclo[4.3.0]non-8-yl]phenyl]-2-oxo-5-oxazolidinyl]methyl]acetamide;

(S)-N-[[3-[3-fluoro-4-[(S,S)-2-(methoxyacetyl)-2,8-diazabicyclo[4.3.0]non-8-yl]phenyl]-2-oxo-5-oxazolidinyl]methyl]acetamide;

(S)-N-[[3-[3-fluoro-4-[(R,R)-2-(methoxyacetyl)-2,8-diazabicyclo[4.3.0]non-8-yl]phenyl]-2-oxo-5-oxazolidinyl]methyl]acetamide;

(S)-N-[[3-[3-fluoro-4-[(R,R)-2-(methoxyacetyl)-2,8-diazabicyclo[4.3.0]non-8-yl]phenyl]-2-oxo-5-oxazolidinyl]methyl]acetamide;

The following additional compounds of Formula II can be prepared using techniques of Formula I and as depicted in Chart VI:

(S)-N-[[3-[3-fluoro-4-[7-(hydroxyacetyl)-2,7-diazaspiro[4.4]nonan-2-yl]phenyl]-2-oxo-5-oxazolidinyl]methyl]acetamide;

(S)-N-[[3-[3-fluoro-4-[7-(acetoxyacetyl)-2,7-diazaspiro[4.4]nonan-2-yl]phenyl]-2-oxo-5-oxazolidinyl]methyl]acetamide;

(S)-N-[[3-[3-fluoro-4-[7-(formyl)-2,7-diazaspiro[4.4]nonan-2-yl]phenyl]-2-oxazolidinyl]methyl]acetamide;

(S)-N-[[3-[3-fluoro-4-[7-(methylsulfonyl)-2,7-diazaspiro[4.4]nonan-2-yl]phenyl]-2-oxo-5-oxazolidinyl]methyl]acetamide;

(S)-N-[[3-[3-fluoro-4-[7-(2-fluoroethyl)-2,7-diazaspiro[4.4]nonan-2-yl]phenyl]-oxo-5-oxazolidinyl]methyl]acetamide;

(S)-N-[[3-[3-fluoro-4-[7-(cyanomethyl)-2,7-diazaspiro[4.4]nonan-2-yl]phenyl]-2-oxo-5-oxazolidinyl]methyl]acetamide;

(S)-N-[[3-[3-fluoro-4-[7-(carbomethoxy)-2,7-diazaspiro[4.4]nonan-2-yl]phenyl]-2-oxo-5-oxazolidinyl]methyl]acetamide;

(S)-N-[[3-[3-fluoro-4-[1-(hydroxyacetyl)-1,7-diazaspiro[4.4]nonan-7-yl]phenyl]-2-oxo-5-oxazolidinyl]methyl]acetamide;

(S)-N-[[3-[3-fluoro-4-[1-(acetoxyacetyl)-1,7-diazaspiro[4.4]nonan-7-yl]phenyl]-2-oxo-5-oxazolidinyl]methyl]acetamide;

(S)-N-[[3-[3-fluoro-4-[1-(formyl)- 1,7-diazaspiro[4.4]nonan-7-yl]phenyl]-2-oxazolidinyl]methyl]acetamide;

(S)-N-[[3-[3-fluoro-4-[1-(methylsulfonyl)- 1,7-diazaspiro[4.4]nonan-7-yl]phenyl]-2-oxo-5-oxazolidinyl]methyl]acetariide;

(S)-N-[[3-[3-fluoro-4-[1-(2-fluoroethyl)-1,7-diazaspiro[4.4]nonan-7-yl]phenyl]-2-oxo-5-oxazolidinyl]methyl]acetamide;

(S)-N-[[3-[3-fluoro-4-[1-(cyanomethyl)-1,7-diazaspiro[4.4]nonan-7-yl]phenyl]-2-oxo-5-oxazolidinyl]methyl]acetamide;

(S)-N-[[3-[3-fluoro-4-[1-(carbomethoxy)-1,7-diazaspiro[4.4]nonan-7-yl]phenyl]-2-oxo-5-oxazolidinyl]methyl]acetamide;

(S)-N-[[3-[3-fluoro-4-[2-aza-7-oxospiro[4.5]decan-2-yl]phenyl]-2-oxo-5-oxazolidinyl]methyl]acetamide;

(S)-N-[[3-[3-fluoro-4-[2-aza-7-(methoxyimino)spiro[4.5]decan-2-yl]phenyl]-2-oxo-5-oxazolidinyl]methyl]acetamide;

(S)-N-[[3-[3-fluoro-4-[2-aza-7-(hydroxyimino)spiro[4.5]decan-2-yl]phenyl]-2-oxo-5-oxazolidinyl]methyl]acetamide; and (S)-N-[[3-[3-fluoro-4-[2-aza-7-oxospiro[4.5]decan-2-yl]phenyl]-2-oxo-5-oxazolidinyl]methyl]acetamide ethylene ketal.

Antibacterial Activity

The oxazolidinone antibacterial agents of this invention have useful activity against a variety of organisms. The in vitro activity of compounds of this invention can be assessed by standard testing procedures such as the determination of minimum inhibitory concentration (MIC) by agar dilution as described in "Methods for Dilution Antimicrobial Susceptibility Tests for Bacteria That Grow Aerobically" (MFT) published January 1983 by the National Committee for Clinical Laboratory Standards, 771 East Lancaster Avenue, Villanova, Pa. 19084, USA. The activity of selected compounds of this invention against *Staphylococcus aureus* and *Streptococcus pneumoniae* are shown in Table 1.

TABLE 1

| Minimum Inhibitory Concentration ($\mu$g/mL) | | |
|---|---|---|
| Example No. | *S. aureus* UC® 9213 | *S. pneumoniae* UC® 9912 |
| 1 | 4 | 2 |
| 2 | 8 | 1 |
| 3 | 4 | <0.5 |
| vancomycin | 1 | 0.5 |

Chart I

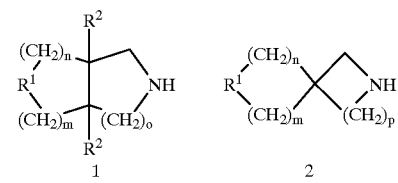

CHART II
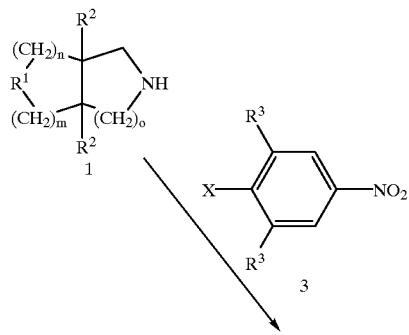
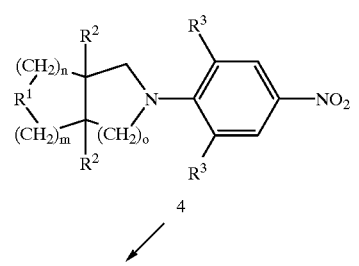
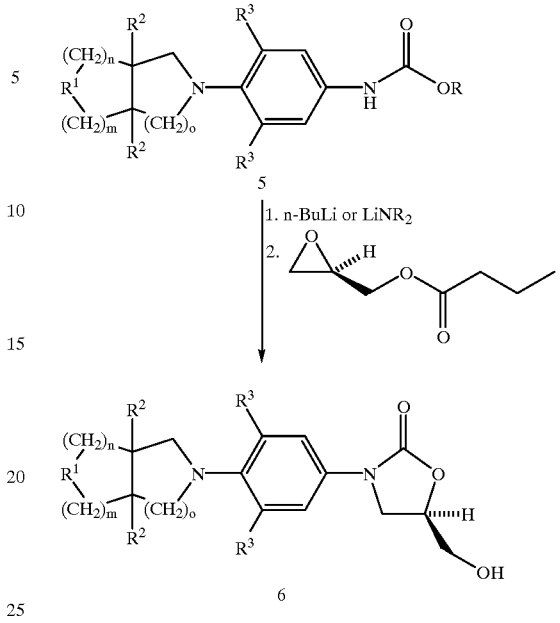
Chart III
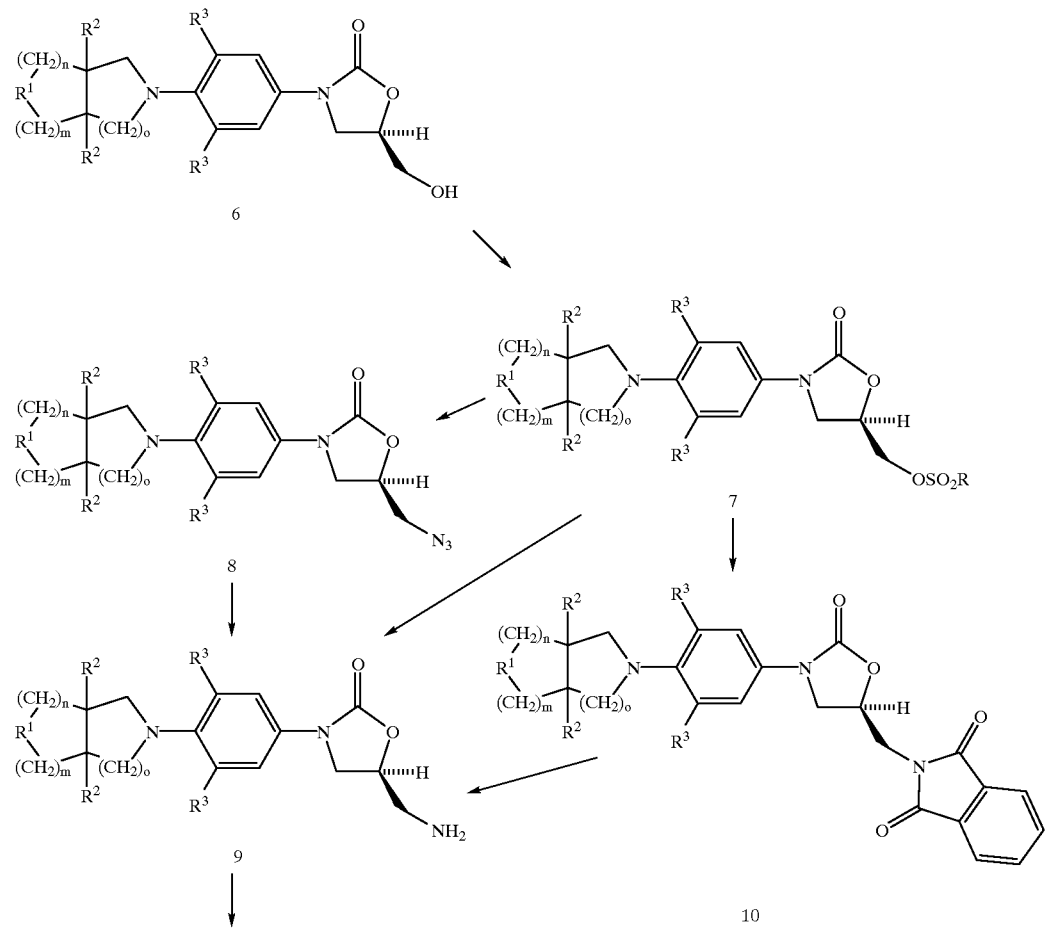

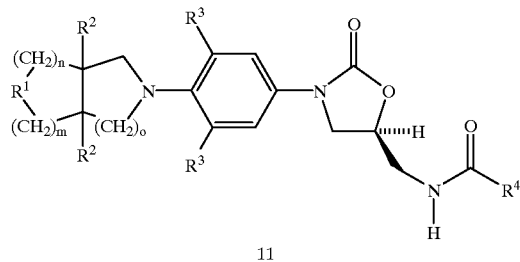
Chart IV
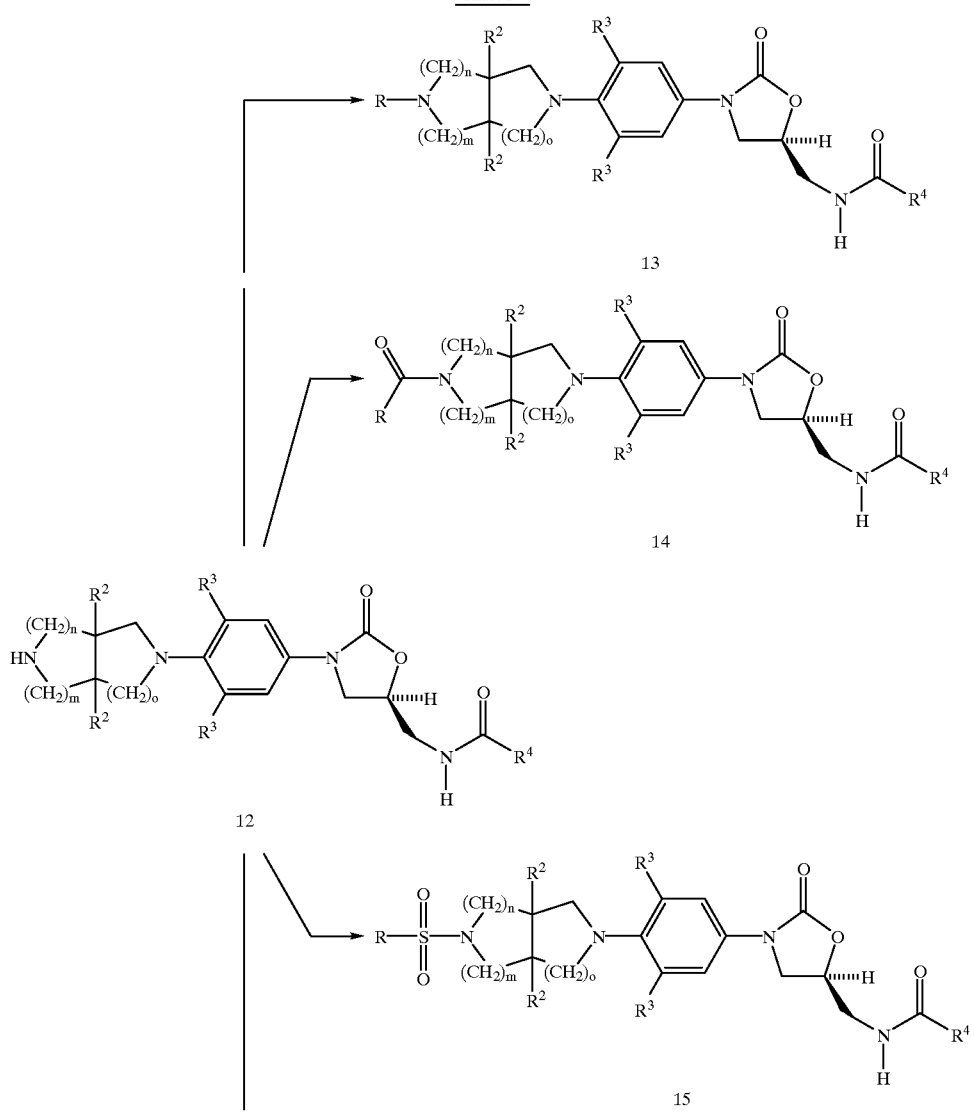

-continued
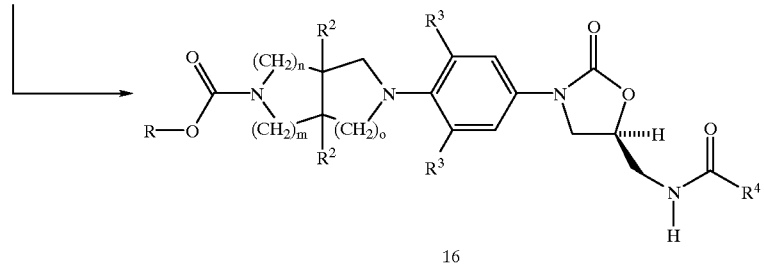
16
Chart V
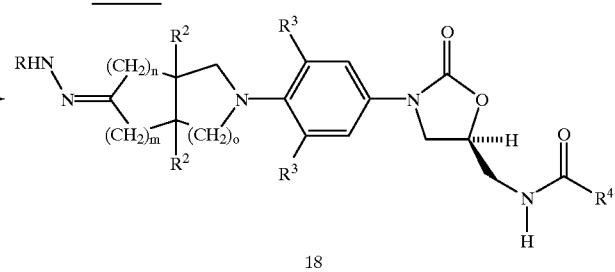
18
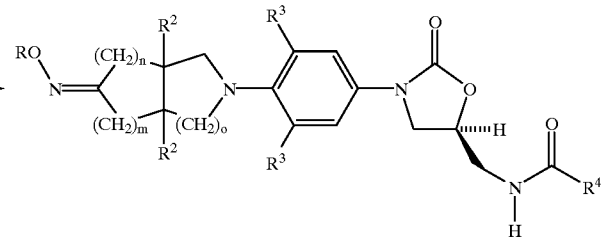
19
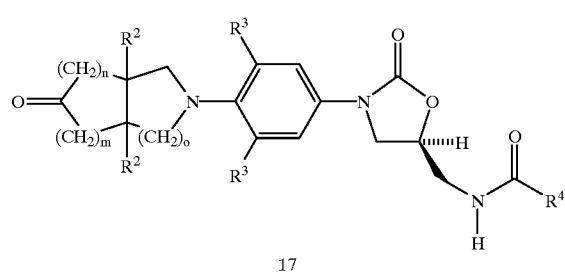
17
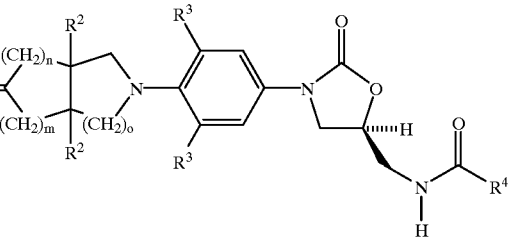
20

-continued

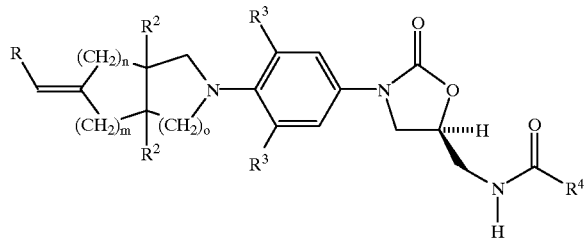
21

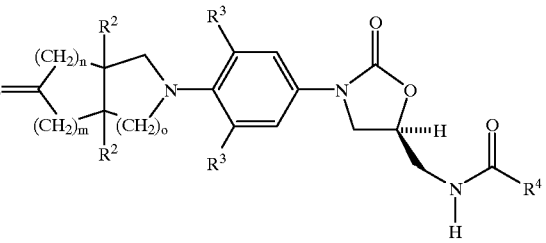
22

Chart VI

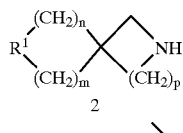
2

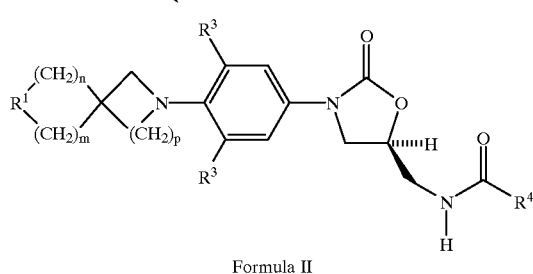
Formula II

What is claimed:
1. A compound of structural Formula I:

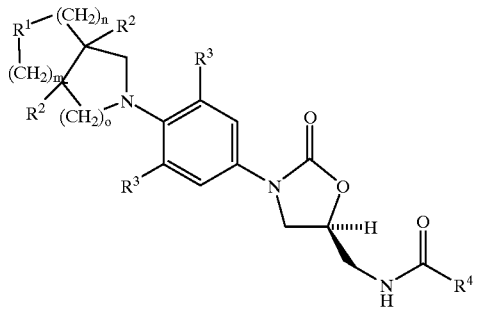
Formula I or a pharmaceutically acceptable salt thereof wherein:

$R^1$ is (a) $NR^5$, $R^2$ is independently H or $CH_3$;

$R^3$ is independently H, F, Cl or methoxy;

$R^4$ is (a) hydrogen,
- (b) $C_1$–$C_8$ alkyl optionally substituted with one or more of the following: F, Cl, hydroxy, $C_1$–$C_8$ alkoxy or $C_1$–$C_8$ acyloxy,
- (c) $C_3$–$C_6$ cycloalkyl,
- (d) amino,
- (e) $C_1$–$C_8$ alkylamino,
- (f) $C_1$–$C_8$ dialkylamino, or
- (g) $C_1$–$C_8$ alkoxy;

$R^5$ is (a) H,
- (b) $C_{1-6}$ alkyl optionally substituted with one or more of the following: Cl, F, CN, OH, $C_{1-4}$ alkoxy, amino, hydroxylamino, alkoxylamino, $C_{1-4}$ acyloxy, $C_{1-4}$ alkylsulfenyl, $C_{1-4}$ alkylsulfinyl, $C_{1-4}$ alkylsulfonyl, aminosulfonyl, $C_{1-4}$ alkylaminosulfonyl, $C_{1-4}$ dialkylaminosulfonyl, 4-morpholinylsulfonyl, phenyl (optionally substituted with one or more of F, Cl, CN, OH, $C_1$–$C_4$alkoxy), 5-isoxazolyl, ethenyloxy or ethynyl,
- (c) $C_{1-6}$ acyl optionally substituted with one or more of the following: Cl, F, OH, SH, $C_{1-4}$ alkoxy, naphthalenoxy and phenoxy (optionally substituted with one or more of the following: Cl, F, OH, $C_1$–$C_4$alkoxy, amino, $C_1$–$C_4$acyl amino, $C_1$–$C_4$alkyl), amino, $C_1$–$C_4$acylamino, hydroxylamino, alkoxylamino, $C_{1-4}$ acyloxy, phenyl, $C_1$–$C_4$alkylcarbonyl, $C_1$–$C_4$alkylamino, $C_1$–$C_4$dialkylamino, $C_1$–$C_4$hydroxyacyloxy, $C_1$–$C_4$alkylsulfenyl, phthalimido, maleimido or succinimido,
- (d) $C_{1-6}$ alkylsulfonyl optionally substituted with one or more of the following: Cl, F, OH, $C_{1-4}$ alkoxy, amino, hydroxylamino, alkoxylamino, $C_{1-4}$ acyloxy or phenyl,
- (e) arylsulfonyl optionally substituted with one or more of the following:

F, Cl, $OCH_3$, OH or $C_{1-4}$ alkyl,
- (f) $C_{1-6}$ alkoxycarbonyl optionally substituted with one or more of the following: Cl, F, OH, $C_{1-4}$ alkoxy, $C_{1-4}$ acyloxy or phenyl,
- (g) aminocarbonyl, $C_{1-6}$ alkylaminocarbonyl or $C_{1-6}$ dialkylaminocarbonyl (where the alkyl groups are optionally substituted with one or more of the following: Cl, F, OH, $C_{1-4}$ alkoxy or phenyl), (h) five- and six-membered heterocycle optionally substituted with one or more of the following: Cl, F, OH, amino or $C_{1-4}$acylamino, $C_{1-4}$ alkylsulfonylamino, $C_{1-4}$ alkoxycarbonylamino, $C_{1-4}$ alkoxy, $C_{1-4}$ acyloxy or $C_{1-4}$alkyl which is optionally substituted with F, OH or $C_{1-4}$ alkoxy, (i) $C_3$–$C_6$cycloalkylcarbonyl optionally substituted with one or more of the following: F, Cl, OH, $C_1$–$C_4$alkoxy or CN, (j) benzoyl optionally substituted with one or more of the following: F, Cl, OH, $C_1$–$C_4$alkoxy, $C_1$–$C_4$alkyl amino or $C_1$–$C_4$acylamino, (k) pyrrolylcarbonyl optionally substituted with one or more of $C_1$–$C_4$alkyl, or (l) $C_1$–$C_2$ acyloxyacetyl where the acyl is optionally substituted with the following:
amino, $C_1$–$C_4$alkylamino, $C_1$–$C_4$dialkylamino, 4-morpholino,
4-aminophenyl, 4-(dialkylamino)phenyl or 4-(glycylamino)phenyl;

$R^6$ is (a) H,
(b) OH,
(c) $C_{1-6}$ alkoxy,
(d) amino, $C_{1-6}$ alkylamino, $C_{1-6}$ dialkylamino, hydroxylamino, or $C_{1-2}$ alkoxylamino all of which is optionally substituted on the nitrogen with: $C_{1-6}$ acyl (optionally substituted with one or two of Cl or OH), $C_{1-6}$ alkylsulfonyl optionally substituted with one or two of Cl or OH), or $C_{1-6}$ alkoxycarbonyl, or
(e) Cl or F;

$R^7$ is (a) H,
(b) $C_{1-6}$ alkyl optionally substituted with one or more of the following: Cl, F, CN, OH, $C_{1-4}$ alkoxy, $C_{1-4}$ acyloxy or amino,
(c) CN, or
(d) phenyl optionally substituted with one or more of the following: Cl, F, OH or $C_{1-4}$ alkoxy; or $R^6$ and $R^7$ taken together are (a) carbonyl or thiocarbonyl group,
(b) ethylene ketal (—OCH$_2$CH$_2$O—), propylene ketal (—OCH$_2$CH$_2$CH$_2$O—), ethylene thioketal (—SCH$_2$CH$_2$S—), propylene thioketal (—SCH$_2$CH$_2$CH$_2$S—), dimethyl ketal, diethyl ketal, dimethyl thioketal or diethyl thioketal,
(c) oxime optionally substituted with H, $C_{1-6}$ alkyl (optionally substituted with Cl, F or $C_{1-4}$ alkoxy), $C_{1-6}$ acyl (optionally substituted with one or more of the following: Cl, F, OH, $C_{1-4}$ alkoxy or $C_{1-4}$ acyloxy),
(d) hydrazone optionally substituted with H, $C_{1-6}$ alkyl (optionally substituted with one or more Cl, F, OH, $C_{1-4}$ alkoxy, $C_{1-4}$ acyloxy, phenyl, $C_{1-6}$ acyl (optionally substituted with one or more of Cl, F, OH, $C_{1-4}$ alkoxy, $C_{1-4}$ acyloxy, phenyl), $C_{1-6}$ alkoxycarbonyl (optionally substituted with one or more of the following: Cl, F, OH, $C_{1-4}$ alkoxy, $C_{1-4}$ acyloxy or phenyl), or $C_{1-6}$ alkylsulfonyl,
(e) imine optionally substituted with H or a $C_{1-6}$ alkyl (optionally substituted with Cl, F, OH, $C_{1-4}$ alkoxy, $C_{1-4}$ acyloxy, or phenyl), or
(f) carbon-carbon double bond optionally substituted with H, $C_{1-4}$ alkoxycarbonyl or $C_{1-4}$ alkyl (optionally substiuted with Cl, F, OH, $C_{1-4}$ alkoxy or phenyl);

m is 0–2; n is 1–3; o is 0–3; and p is 1–3.

2. The compound of claim 1 wherein one $R^3$ is fluorine and the other is hydrogen.

3. The compound of claim 1 wherein each $R^3$ is fluorine.

4. The compound of claim 1 wherein $R^4$ is hydrogen, methyl, difluoromethyl, dichloromethyl, hydroxymethyl or methoxy.

5. The compound of claim 4 wherein $R^4$ is methyl, difluoromethyl, dichloromethyl or methoxy.

6. The compound of claim 5 wherein $R^4$ is methyl.

7. The compound of claim 1 wherein $R^5$ is hydroxyacetyl.

8. The compound of claim 1 which is (a) (S)-N-[[3-[3-fluoro-4-[cis-3-(carbobenzyloxy)-3,7-diazabicyclo[3.3.0]octan-7-yl]phenyl]-2-oxo-5-oxazolidinyl]methyl]acetamide (Example 1), (b) (S)-N-[[3-[3-fluoro-4-[cis-3-(benzyloxyacetyl)-3,7-diazabicyclo[3.3.0]octan-7-yl]phenyl]-2-oxo-5-oxazolidinyl]methyl]acetamide (Example 2), or (c) (S)-N-[[3-[3-fluoro-4-[cis-3-(hydroxyacetyl)-3,7-diazabicyclo[3.3.0]octan-7-yl]phenyl]-2-oxo-5-oxazolidinyl]methyl]acetamide (Example 3), (d) (S)-N-[[3-[3-fluoro-4-[cis-3-(5-isoxazolinoyl)-3,7-diazabicyclo[3.3.0]octan-7-yl]phenyl]-2-oxo-5-oxazolidinyl]methyl]acetamide (Example 4), (e) (S)-N-[[3-[3-fluoro-4-[cis-3-(2-indolylcarbonyl)-3,7-diazabicyclo[3.3.0]octan-7-yl]phenyl]-2-oxo-5-oxazolidinyl]methyl]acetamide (Example 5), (f) (S)-N-[[3-[3-fluoro-4-[cis-3-(carbomethoxy)-3,7-diazabicyclo[3.3.0]octan-7-yl]phenyl]-2-oxo-5-oxazolidinyl]methyl]acetamide (Example 6), (g) (S)-N-[[3-[3-fluoro4-[cis-3-(formyl)-3,7-diazabicyclo[3.3.0]octan-7-yl]phenyl]-2-oxo-5-oxazolidinyl]methyl]acetamide (Example 7), (h) (S)-N-[[3-[3-fluoro-4-[cis-3-(acetyl)-3,7-diazabicyclo[3.3.0]octan-7-yl]phenyl]-2-oxo-5-oxazolidinyl]methyl]acetamide (Example 8), (i) (S)-N-[[3-[4-[cis-3-(carbobenzyloxy)-3,7-diazabicyclo[3.3.0]octan-7-yl]phenyl]-2-oxo-5-oxazolidinyl]methyl]acetamide (Example 9), (j) (S)-N-[[3-[3-fluoro-4-[cis-2-(carbobenzyloxy)-2,8-diazabicyclo[4.3.0]nonan-8-yl]phenyl]-2-oxo-5-oxazolidinyl]methyl]acetamide (Example 10), (k) (S)-N-[[3-[3-fluoro4-[cis-2-(carbomethoxy)-2,8-diazabicyclo[4.3.0]nonan-8-yl]phenyl]-2-oxo-5-oxazolidinyl]methyl]acetamide (Example 11), (l) (S)-N-[[3-[3-fluoro-4-[cis-2-(acetoxyacetyl)-2,8-diazabicyclo[4.3.0]nonan-8-yl]phenyl]-2-oxo-5-oxazolidinyl]methyl]acetamide (Example 12), or (m) (S)-N-[[3-[3-fluoro-4-[cis-2-(hydroxyacetyl)-2,8-diazabicyclo[4.3.0]nonan- 8-yl]phenyl]-2-oxo-5-oxazolidinyl]methyl]acetamide (Example 13).

9. A method for treating microbial infections in warm-blooded animals by administering to a patient in need thereof an effective amount of a compound of Formula I of claim 1.

10. The method of claim 9 wherein the compound of Formula I is administered in an effective amount of from about 0.1 to about 100 mg/kg of body weight/day.

11. The method of claim 10 wherein the compound of Formula I is administered in an effective amount of from about 3.0 to about 50 mg/kg of body weight/day.

* * * * *